United States Patent
Lim et al.

(10) Patent No.: US 11,422,425 B2
(45) Date of Patent: Aug. 23, 2022

(54) ELECTROCHROMIC DEVICE COMPRISING ELECTROCHROMIC COMPOUND AND MANUFACTURING METHOD THEREFOR

(71) Applicant: LG CHEM, LTD., Seoul (KR)

(72) Inventors: Bogyu Lim, Daejeon (KR); Jiyoung Lee, Daejeon (KR); Ji Hoon Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 540 days.

(21) Appl. No.: 16/607,237

(22) PCT Filed: Jul. 4, 2018

(86) PCT No.: PCT/KR2018/007567
§ 371 (c)(1),
(2) Date: Oct. 22, 2019

(87) PCT Pub. No.: WO2019/013486
PCT Pub. Date: Jan. 17, 2019

(65) Prior Publication Data
US 2020/0301230 A1    Sep. 24, 2020

(30) Foreign Application Priority Data
Jul. 10, 2017 (KR) .................. 10-2017-0087179

(51) Int. Cl.
*C09K 9/02* (2006.01)
*C07D 495/04* (2006.01)
*G02F 1/1516* (2019.01)

(52) U.S. Cl.
CPC .......... *G02F 1/1516* (2019.01); *C07D 495/04* (2013.01); *C09K 9/02* (2013.01); *C09K 2211/1011* (2013.01); *C09K 2211/1018* (2013.01)

(58) Field of Classification Search
CPC . G02F 1/1516; C09K 9/02; C09K 2211/1011; C09K 2211/1018; C07D 495/04
See application file for complete search history.

(56) References Cited

U.S. PATENT DOCUMENTS

| 6,143,433 A | 11/2000 | Murata et al. |
| 6,344,918 B1 | 2/2002 | Berneth et al. |
| 7,445,855 B2 | 11/2008 | Mackenzie et al. |

(Continued)

FOREIGN PATENT DOCUMENTS

| CN | 102336784 A | 2/2012 |
| CN | 103664646 A | 3/2014 |

(Continued)

OTHER PUBLICATIONS

Zhao et al. "Derivatives of 4,9-Dihydro-s-indaceno[1,2-b:5,6-b']dithiophene-4,9-dione: Synthesis and Properties" J. Org. Chem., 72(17):6364-6371 (2007).

(Continued)

*Primary Examiner* — Bijan Ahvazi
(74) *Attorney, Agent, or Firm* — Myers Bigel, P.A.

(57) ABSTRACT

The present application relates to an electrochromic device comprising a compound for electrochromism represented by Chemical Formula 1, and a method for manufacturing same.

16 Claims, 5 Drawing Sheets

(56) References Cited

U.S. PATENT DOCUMENTS

| | | | |
|---|---|---|---|
| 8,007,926 | B2 | 8/2011 | Thompson et al. |
| 9,190,626 | B2 | 11/2015 | Joo et al. |
| 9,391,281 | B2 | 7/2016 | Lee et al. |
| 9,540,374 | B2 | 1/2017 | Park et al. |
| 9,748,489 | B2 | 8/2017 | Kim et al. |
| 9,954,181 | B2 | 4/2018 | Heo et al. |
| 10,326,083 | B2 | 6/2019 | Yagi et al. |
| 10,381,569 | B2 | 8/2019 | Xia et al. |
| 10,662,313 | B2 | 5/2020 | Choi et al. |
| 10,756,276 | B2 | 8/2020 | Lim et al. |
| 2009/0200926 | A1 | 8/2009 | Lee et al. |
| 2011/0049367 | A1 | 3/2011 | Forrest et al. |
| 2012/0013966 | A1 | 1/2012 | Das et al. |
| 2012/0119195 | A1 | 5/2012 | Sagisaka et al. |
| 2013/0042918 | A1 | 2/2013 | Evans et al. |
| 2013/0105768 | A1 | 5/2013 | Leem et al. |
| 2014/0131627 | A1 | 5/2014 | Wang et al. |
| 2014/0158949 | A1 | 6/2014 | Wang et al. |
| 2014/0252279 | A1 | 9/2014 | Wang et al. |
| 2015/0041727 | A1 | 2/2015 | Wang et al. |
| 2016/0372680 | A1 | 12/2016 | Lim et al. |
| 2017/0018724 | A1 | 1/2017 | Tsuyama et al. |
| 2017/0210752 | A1 | 7/2017 | Mitchell et al. |
| 2019/0363262 | A1 | 11/2019 | Lim et al. |
| 2019/0378993 | A1 | 12/2019 | Lim et al. |
| 2020/0301230 | A1 | 9/2020 | Lim et al. |

FOREIGN PATENT DOCUMENTS

| | | | | |
|---|---|---|---|---|
| CN | | 104557968 A | 4/2015 | |
| JP | | 2009155648 A | 7/2009 | |
| JP | | 2015059109 A | 3/2015 | |
| JP | | 2016065218 A | 4/2016 | |
| KR | | 1020010112380 | 12/2001 | |
| KR | | 1020080075663 A | 8/2008 | |
| KR | | 1020110132858 | 12/2011 | |
| KR | | 1020120043009 | 5/2012 | |
| KR | | 1020120043009 A | 5/2012 | |
| KR | | 1020130047367 A | 5/2013 | |
| KR | | 1020140063579 | 5/2014 | |
| KR | | 1020140063579 A | 5/2014 | |
| KR | | 1020140063608 A | 5/2014 | |
| KR | | 1020140088571 | 7/2014 | |
| KR | | 1020140088571 A | 7/2014 | |
| KR | | 1020140135749 | 11/2014 | |
| KR | | 1020140135749 A | 11/2014 | |
| KR | | 1020150113629 A | 10/2015 | |
| KR | | 1020150113631 A | 10/2015 | |
| KR | | 1020150121661 A | 10/2015 | |
| KR | | 20160097766 A | * 8/2016 | ........... C07D 495/04 |
| KR | | 1020160097766 | 8/2016 | |
| KR | | 1020160097766 A | 8/2016 | |
| KR | | 1020170003234 A | 1/2017 | |
| KR | | 1020170038037 A | 4/2017 | |
| WO | | 2019066553 A2 | 4/2019 | |

OTHER PUBLICATIONS

International Search Report corresponding to PCT/KR2018/007567; dated Oct. 16, 2018 (5 pages included English translation).
Chemical Abstract Service STN Database, Registry No. 1817646-68-6 [Entered STN: Oct. 30, 2015], (Year: 2015).
International Search Report corresponding to PCT/KR2018/009524; dated Mar. 7, 2019 (5 pages, including English translation).
International Search Report of the International Searching Authority corresponding to PCT/KR2018/003091; dated Jun. 22, 2018 (6 pages, including English translation).
International Search Report of the International Searching Authority corresponding to PCT/KR2018/010895; dated Jan. 2, 2019 (5 pages, including English translation).
Lee, Seung-Hoon, et al., "Highly π-extended small molecules with bis(alkylthio)methylene side chains for organic field-effect transistors", Journal of Materials Chemistry C, 6, 2018, 7604-7611.
Lin, Yuze, et al., "A Facile Planar Fused-Ring Electron Acceptor for As-Cast Polymer Solar Cells with 8.71% Efficiency", Journal of the American Chemical Society, 138(9), 2016, 2973-2976.
Tang, C. W., "Two-layer organic photovoltaic cell", Applied Physics Letters 48(2), 1986, 183-185.
Yu, G., et al., "Polymer Photovoltaic Cells: Enhanced Efficiencies via a Network of Internal Donor-Acceptor Heterojunctions", Science, 270(5243), 1995, 1789-1791.

* cited by examiner

ELECTROCHROMIC DEVICE COMPRISING ELECTROCHROMIC COMPOUND AND MANUFACTURING METHOD THEREFOR

CROSS REFERENCE TO RELATED APPLICATIONS

This application is a 35 U.S.C. § 371 national stage application of PCT International Application No. PCT/KR2018/007567, filed Jul. 4, 2018, which claims priority from Korean Patent Application No. 10-2017-0087179, filed Jul. 10, 2017, the contents of which are incorporated herein in their entireties by reference. The above-referenced PCT International Application was published in the Korean language as International Publication No. WO 2019/013486 on Jan. 17, 2019.

TECHNICAL FIELD

The present application relates to an electrochromic device comprising a compound for electrochromism.

BACKGROUND ART

An electrochromism technology is a technology changing colors of a material using an electrochemical reaction, and refers to properties of colors of a material changing reversibly while electron density changes with intercalation or deintercalation of cations in an electrode structure by an electrochemical redox reaction occurring from changes in the applied voltage.

An electrochromic device is a device having color changes by an electrochemical reaction. When a potential difference occurs in an electrochromic device due to an external electrical simulation, ions or electrons included in an electrolyte migrate into an electrochromic layer causing a redox reaction. Colors of the electrochromic device changes by the redox reaction of the electrochromic layer. A reductive electrochromic material means a material colored when a reduction reaction (cathodic reaction) occurs and bleached when an oxidation reaction (anodic reaction) occurs. An oxidative electrochromic material means a material colored when an oxidation reaction occurs and bleached when a reduction reaction occurs.

An electrochromic device has been very actively studied in applications such as optical shutters, displays, smart windows or electrochromic mirrors for automobiles due to exhibiting a high contrast ratio, a simple transmittance control by a driving voltage, a low driving voltage, bistability and a wide viewing angle.

DISCLOSURE

Technical Problem

The present application is directed to providing an electrochromic device comprising a compound for electrochromism having excellent stability.

Technical Solution

One embodiment of the present application provides an electrochromic device comprising a substrate; a first electrode formed on the substrate; a second electrode provided opposite to the first electrode; an electrolyte layer formed between the first electrode and the second electrode; and an electrochromic layer formed between the electrolyte layer and the second electrode, wherein one or more layers of the electrochromic layer comprise a compound for electrochromism according to the following Chemical Formula 1.

[Chemical Formula 1]

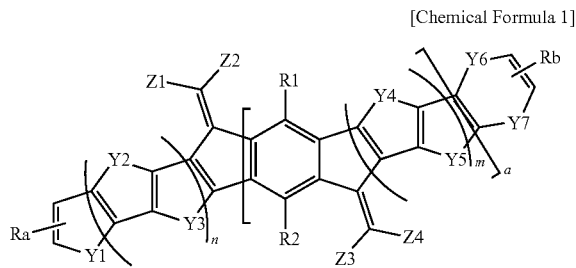

In Chemical Formula 1,

Ra and Rb are the same as or different from each other, and each independently a group functioning as an electron acceptor, Y1 to Y5 are the same as or different from each other, and each independently CRR', NR, O, SiRR', PR, S, GeRR', Se or Te, Y6 and Y7 are different from each other, and each independently a direct bond, NR, O, SiRR', PR, S, GeRR', Se or Te, a is 0 or 1, when a is 0, Y6 is a direct bond, and Y7 is CRR', NR, O, SiRR', PR, S, GeRR', Se or Te, when a is 1, Y7 is a direct bond, and Y6 is CRR', NR, O, SiRR', PR, S, GeRR', Se or Te, n and m are each an integer of 0 to 5, when n and m are 2 or greater, structures in the parentheses are the same as or different from each other, Z1 to Z4 are the same as or different from each other, and each independently CRR'R", NRR', OR, SiRR'R", PRR', SR, GeRR'R", SeR or TeR, R1, R2, R, R' and R" are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heteroaryl group.

Another embodiment of the present application provides a method for manufacturing an electrochromic device comprising preparing a substrate; forming a first electrode on the substrate; forming a second electrode opposite to the first electrode; forming an electrolyte layer between the first electrode and the second electrode; and forming an electrochromic layer between the electrolyte layer and the second electrode, wherein one or more layers of the electrochromic layer comprise the compound for electrochromism according to Chemical Formula 1.

Advantageous Effects

A compound for electrochromism according to one embodiment of the present application is capable of introducing sulfur (S) and the like to an alkyl chain, and enhances electron migration by chalcogen-chalcogen interactions in the molecule, and as a result, is capable of enhancing an electrochromic response rate and electrochromic conversion efficiency (coloration efficiency).

The compound for electrochromism according to one embodiment of the present application has excellent oxidation stability, and has an excellent lifetime when used in an electrochromic device.

REFERENCE NUMERAL

Figure 1:
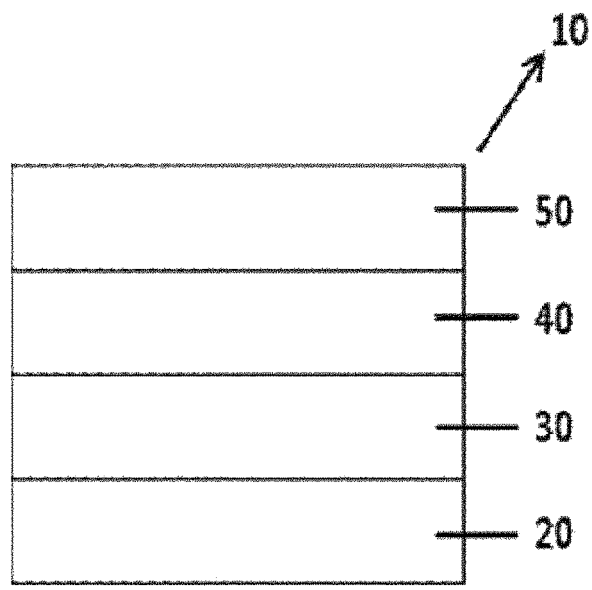
FIG. 1 is a side view of an electrochromic device according to one embodiment of the present application.

10: Electrochromic Device
20: First Electrode
30: Electrolyte Layer
40: Electrochromic Layer
50: Second Electrode

MODE FOR DISCLOSURE

Hereinafter, the present application will be described in more detail.

Embodiments of the present disclosure will be described in detail with reference to accompanying drawings so that those skilled in the art readily implement the present disclosure. However, the present disclosure may be embodied in various different forms, and is not limited to the embodiments described herein.

One embodiment of the present application provides an electrochromic device comprising a substrate; a first electrode formed on the substrate; a second electrode provided opposite to the first electrode; an electrolyte layer formed between the first electrode and the second electrode; and an electrochromic layer formed between the electrolyte layer and the second electrode, wherein one or more layers of the electrochromic layer comprise a compound for electrochromism according to Chemical Formula 1.

In the present specification, a description of a certain part "including" certain constituents means capable of further including other constituents, and does not exclude other constituents unless particularly stated on the contrary.

In the present specification, a description of a certain member being placed "on" another member includes not only a case of the one member adjoining the another member but a case of still another member being present between the two members.

In the present application, the term "substituted or unsubstituted" means being substituted with one, two or more substituents selected from the group consisting of deuterium; a halogen group; a nitrile group; a nitro group; an imide group; an amide group; a carbonyl group; an ester group; a hydroxyl group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a siloxane group; a boron group; an amine group; an arylphosphine group; a phosphine oxide group; an aryl group; and a heteroaryl group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present application, ─┼─ means a site bonding to other substituents or bonding sites.

In the present application, examples of the halogen group may include fluorine, chlorine, bromine or iodine.

In the present application, the number of carbon atoms of the imide group is not particularly limited, but is preferably from 1 to 30.

In the present application, in the amide group, nitrogen of the amide group may be substituted with hydrogen, a linear, branched or cyclic alkyl group having 1 to 30 carbon atoms, or an aryl group having 6 to 30 carbon atoms.

In the present application, the number of carbon atoms of the carbonyl group is not particularly limited, but is preferably from 1 to 30.

In the present application, in the ester group, carbon or oxygen of the ester group may be substituted with a linear, branched or cyclic alkyl group having 1 to 25 carbon atoms, or an aryl group having 6 to 30 carbon atoms.

In the present application, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methyihexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methyihexyl, 5-methyihexyl and the like, but are not limited thereto.

In the present application, the cycloalkyl group is not particularly limited, but preferably has 3 to 30 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present application, the alkoxy group may be linear, branched or cyclic. The number of carbon atoms of the alkoxy group is not particularly limited, but is preferably from 1 to 30. Specific examples thereof may include methoxy, ethoxy, n-propoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present application, the amine group may be selected from the group consisting of —NH$_2$; an alkylamine group; an N-arylalkylamine group; an arylamine group; an N-arylheteroarylamine group; an N-alkylheteroarylamine group and a heteroarylamine group, and although particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group and the like, but are not limited thereto.

In the present application, the alkyl group in the alkylamine group, the N-arylalkylamine group, the alkylthioxy group, the alkylsulfoxy group and the N-alkylheteroarylamine group is the same as the examples of the alkyl group described above.

In the present application, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present application, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present application, the boron group may be —BR$_{100}$R$_{200}$, and R$_{100}$ and R$_{200}$ are the same as or different from each other and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present application, specific examples of the phosphine oxide group may include a diphenylphosphine oxide group, a dinaphthylphosphine oxide group and the like, but are not limited thereto.

In the present application, the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthryl group, a pyrenyl group, a perylenyl group, a chrysenyl group, a fluorenyl group and the like, but are not limited thereto.

In the present application, the aryl group in the aryloxy group, the arylthioxy group, the arylsulfoxy group, the N-arylalkylamine group, the N-arylheteroarylamine group and the arylphosphine is the same as the examples of the aryl group described above.

In the present application, examples of the arylamine group include a substituted or unsubstituted monoarylamine group, a substituted or unsubstituted diarylamine group, or a substituted or unsubstituted triarylamine group. The aryl group in the arylamine group may be a monocycle aryl group or a polycyclic aryl group. The arylamine group including two or more aryl groups may include monocycle aryl groups, polycyclic aryl groups, or both monocycle aryl groups and polycyclic aryl groups. For example, the aryl group in the arylamine group may be selected from among the examples of the aryl group described above.

In the present application, the heterocyclic group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heterocyclic group may be monocycle or polycyclic. Examples of heterocyclic group may include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present application, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, polycyclic heteroaryl groups, or both monocyclic heteroaryl groups and polycyclic heteroaryl groups. For example, the heteroaryl group in the heteroarylamine group may be selected from among the examples of the heteroaryl group described above.

In the present application, examples of the heteroaryl group in the N-arylheteroarylamine group and the N-alkylheteroarylamine group are the same as the examples of the heteroaryl group described above.

In the present specification, examples of the heteroaryl group in the N-arylheteroarylamine group and the N-alkylheteroarylamine group are the same as the examples of the heteroaryl group described above.

In one embodiment of the present specification, n and m are each an integer of 0 to 5.

In one embodiment of the present specification, n and m are each an integer of 0 to 4.

In one embodiment of the present specification, n and m are each an integer of 0 to 3.

In one embodiment of the present specification, n and m are each an integer of 0 to 2.

In one embodiment of the present specification, n and m are each 0 or 1.

In one embodiment of the present specification, n and m are the same as each other, and each 0 or 1.

In one embodiment of the present specification, the compound represented by Chemical Formula 1 may be symmetrical on both sides with respect to the benzene ring.

In one embodiment of the present specification, the compound represented by Chemical Formula 1 may be represented by the following Chemical Formula 2 or 3.

[Chemical Formula 2]

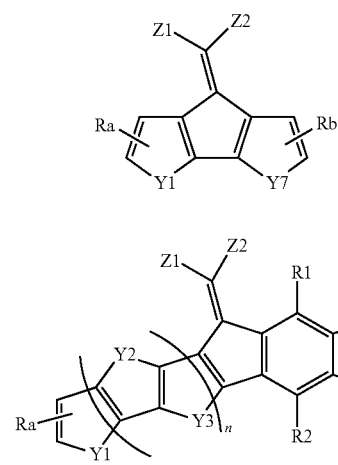

[Chemical Formula 3]

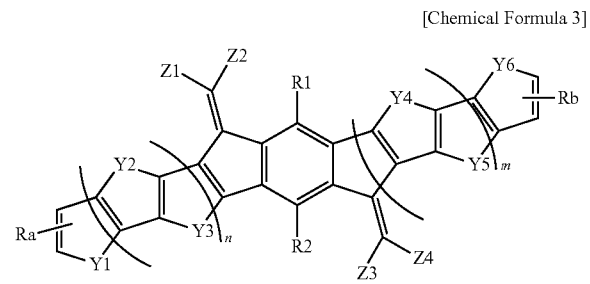

In Chemical Formula 2 or 3,

Ra and Rb are the same as or different from each other, and each independently a group functioning as an electron acceptor, Y1 to Y7 are the same as or different from each other, and each independently CRR', NR, O, SiRR', PR, S, GeRR', Se or Te, n and m are each an integer of 0 to 5, when n and m are 2 or greater, structures in the parentheses are the same as or different from each other, Z1 to Z4 are the same as or different from each other, and each independently CRR'R", NRR', OR, SiRR'R", PRR', SR, GeRR'R", SeR or TeR, and R1, R2, R, R' and R" are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In one embodiment of the present specification, the compound represented by Chemical Formula 3 may be represented by the following Chemical Formula 1-1 or Chemical Formula 1-2.

[Chemical Formula 1-1]

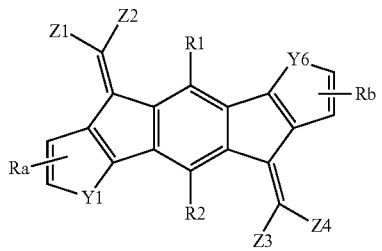

[Chemical Formula 1-2]

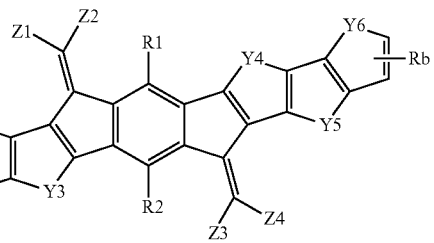

In Chemical Formula 1-1 or Chemical Formula 1-2,

Ra and Rb are the same as or different from each other, and each independently a group functioning as an electron acceptor, Y1 to Y6 are the same as or different from each other, and each independently CRR', NR, O, SiRR', PR, S, GeRR', Se or Te, Z1 to Z4 are the same as or different from each other, and each independently CRR'R", NRR', OR, SiRR'R", PRR', SR, GeRR'R", SeR or TeR, and R1, R2, R, R' and R" are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In one embodiment of the present specification, Ra and Rb may be any one of the following structures.

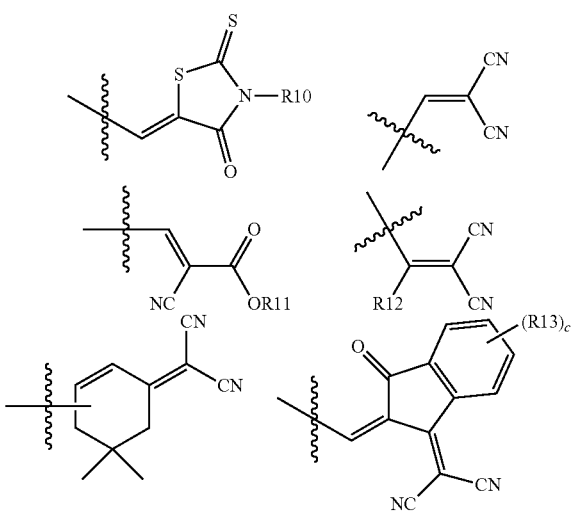

In the structures, c is an integer of 1 to 4, when c is 2 or greater, structures in the two or more parentheses are the same as or different from each other, and R10 to R13 are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In one embodiment of the present specification, R1 and R2 are the same as or different from each other, and each independently hydrogen; a halogen group; a substituted or unsubstituted alkyl group; a substituted or unsubstituted alkoxy group; a substituted or unsubstituted aryl group; or a substituted or unsubstituted heterocyclic group.

In one embodiment of the present specification, R1 and R2 are hydrogen.

In one embodiment of the present specification, R10 to R13 are the same as or different from each other, and each independently hydrogen; a halogen group; a nitrile group; an amide group; a hydroxyl group; a substituted or unsubstituted alkyl group; a substituted or unsubstituted cycloalkyl group; a substituted or unsubstituted alkoxy group; a substituted or unsubstituted aryl group; or a substituted or unsubstituted heterocyclic group.

In one embodiment of the present specification, R10 to R13 are the same as or different from each other, and each independently hydrogen; a halogen group; a substituted or unsubstituted alkyl group; a substituted or unsubstituted aryl group; or a substituted or unsubstituted heterocyclic group.

In one embodiment of the present specification, R10 to R13 are the same as or different from each other, and each independently hydrogen; or a substituted or unsubstituted alkyl group.

In one embodiment of the present specification, R10 is a substituted or unsubstituted alkyl group.

In one embodiment of the present specification, R10 is a substituted or unsubstituted alkyl group having 1 to 30 carbon atoms.

In one embodiment of the present specification, R10 is a substituted or unsubstituted alkyl group having 1 to 20 carbon atoms.

In one embodiment of the present specification, R10 is a substituted or unsubstituted alkyl group having 1 to 10 carbon atoms.

In one embodiment of the present specification, R10 is an alkyl group having 1 to 10 carbon atoms.

In one embodiment of the present specification, R11 to R13 are hydrogen.

In one embodiment of the present specification, Ra and Rb are each

and R13 and c are the same as described above.

In one embodiment of the present specification, Ra and Rb are each

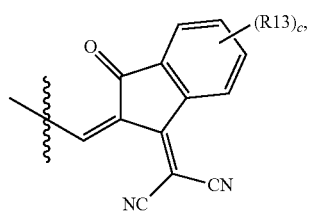

and R13 is hydrogen.

In one embodiment of the present specification, Ra and Rb are each

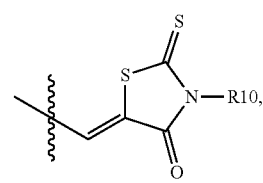

and R10 is the same as described above.

In one embodiment of the present specification, Ra and Rb are each

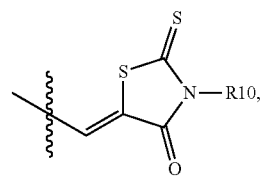

and R10 is an alkyl group having 1 to 10 carbon atoms.

In one embodiment of the present specification, Chemical Formula 1 may be represented by any one of the following Chemical Formulae 1-11 to 1-19.
[Chemical Formula 1-11]
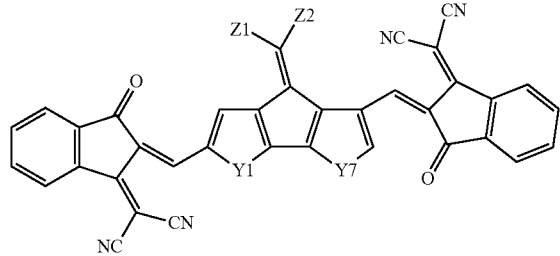
[Chemical Formula 1-12]
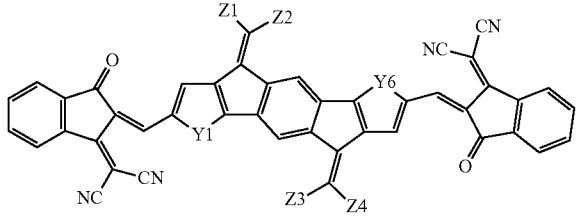
[Chemical Formula 1-13]
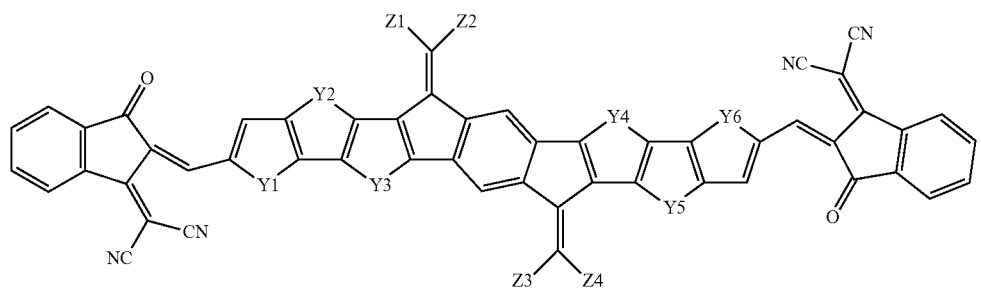
[Chemical Formula 1-14]
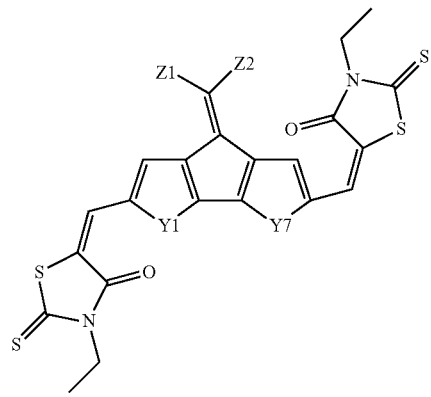
[Chemical Formula 1-15]
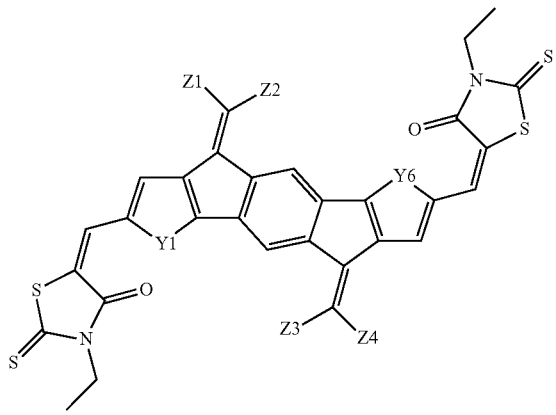
[Chemical Formula 1-16]
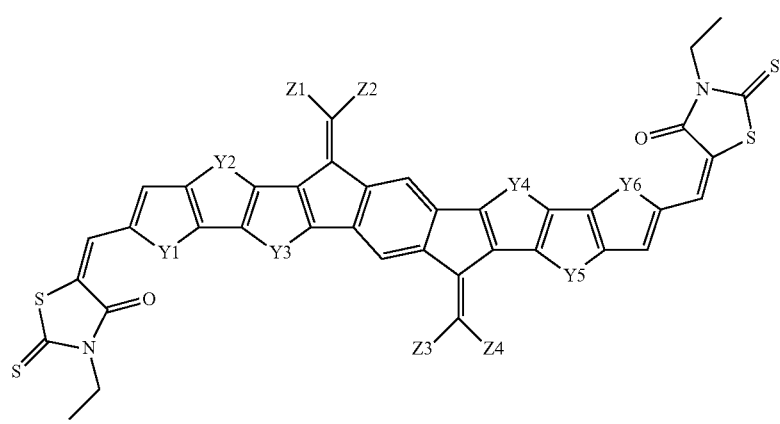

[Chemical Formula 1-17]

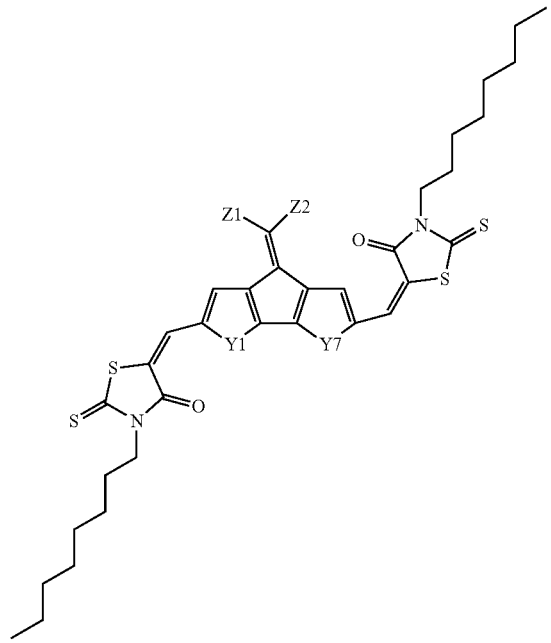

[Chemical Formula 1-18]

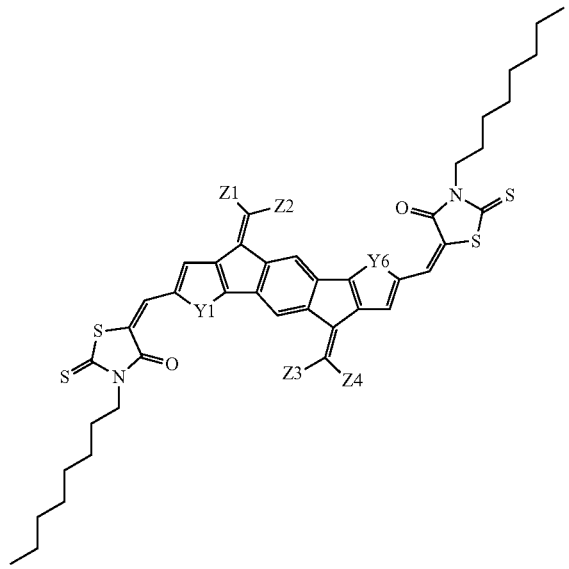

[Chemical Formula 1-19]

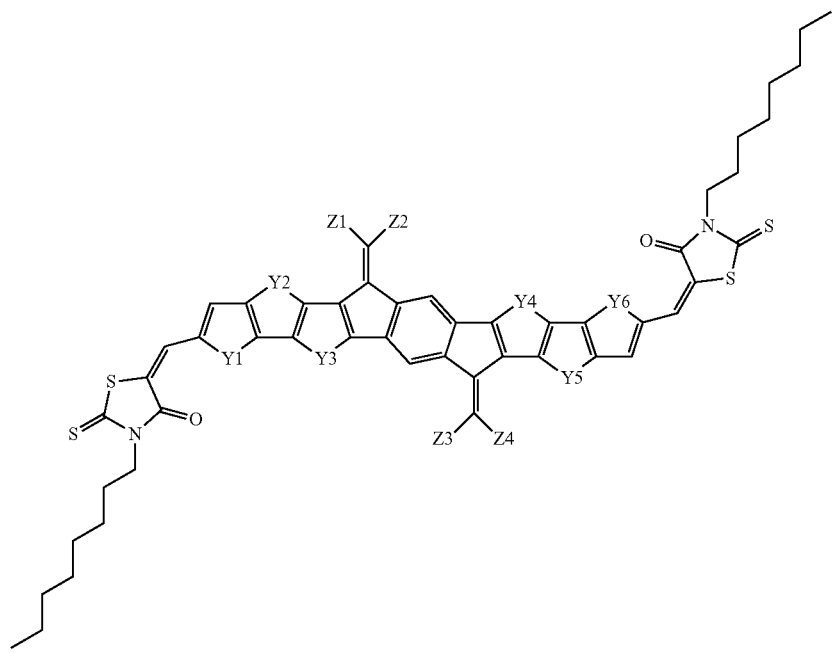

Y1 to Y7 are the same as or different from each other, and each independently CRR', NR, O, SiRR', PR, S, GeRR', Se or Te, Z1 to Z4 are the same as or different from each other, and each independently CRR'R", NRR', OR, SiRR'R", PRR', SR, GeRR'R", SeR or TeR, and R, R' and R" are the same as or different from each other, and each independently hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group.

In one embodiment of the present specification, Y1 to Y7 are the same as or different from each other and each independently CRR', NR, O or S, and R and R' are the same as described above.

In one embodiment of the present specification, Y1 to Y7 are the same as or different from each other and each independently NR or S, and R is the same as described above.

In one embodiment of the present specification, Y1 to Y7 are S.

In one embodiment of the present specification, Z1 to Z4 are the same as or different from each other and each independently CRR'R", NRR', OR or SR, and R, R' and R" are the same as described above.

In one embodiment of the present specification, Z1 to Z4 are the same as or different from each other and each independently O or SR, and R is the same as described above.

In one embodiment of the present specification, Z1 to Z4 are the same as or different from each other and each independently SR, and R is the same as described above.

In one embodiment of the present specification, Z1 to Z4 are the same as or different from each other and each independently SR, and R is a substituted or unsubstituted alkyl group; a substituted or unsubstituted aryl group; or a substituted or unsubstituted heterocyclic group.

In one embodiment of the present specification, Z1 to Z4 are the same as or different from each other and each independently SR, and R is an alkyl group substituted with a substituted or unsubstituted heterocyclic group; an alkyl group substituted with a substituted or unsubstituted aryl group; or a linear or branched alkyl group.

In one embodiment of the present specification, Z1 to Z4 are the same as or different from each other and each independently SR, and R is an alkyl group substituted with a heterocyclic group substituted with an alkyl group; an alkyl group substituted with an aryl group substituted with an alkyl group; or an alkyl group having 1 to 30 carbon atoms.

In one embodiment of the present specification, Z1 to Z4 are the same as or different from each other and each independently SR, and R is an alkyl group substituted with a heterocyclic group substituted with an alkyl group; an alkyl group substituted with an aryl group substituted with an alkyl group; or an alkyl group having 1 to 20 carbon atoms.

In one embodiment of the present specification, Z1 to Z4 are the same as or different from each other and each independently SR, and R is an alkyl group substituted with a heterocyclic group substituted with an alkyl group having 1 to 15 carbon atoms; an alkyl group substituted with an aryl group substituted with an alkyl group having 1 to 15 carbon atoms; or an alkyl group having 1 to 15 carbon atoms.

Particularly, when a structure of S-R is introduced to Z1 to Z4, intermolecular aggregation may be induced by a strong interaction between S, which leads to an advantage of accelerating a charge carrier transfer between the molecules.

In one embodiment of the present specification, Chemical Formula 1 may be represented by any one of the following compounds.

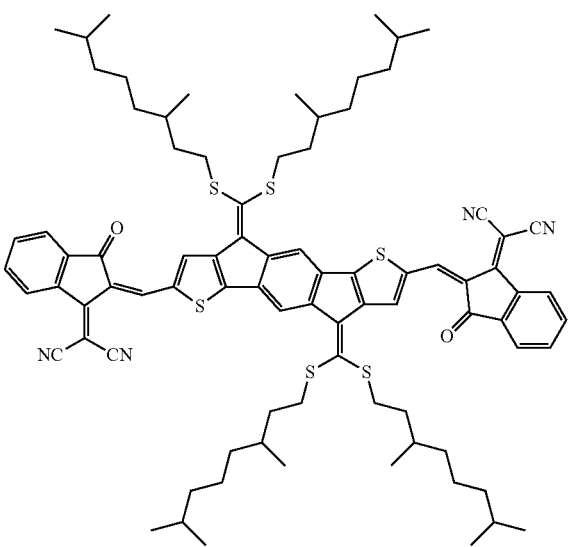

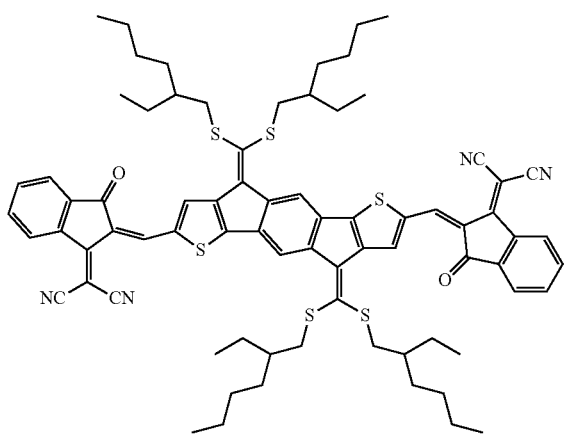

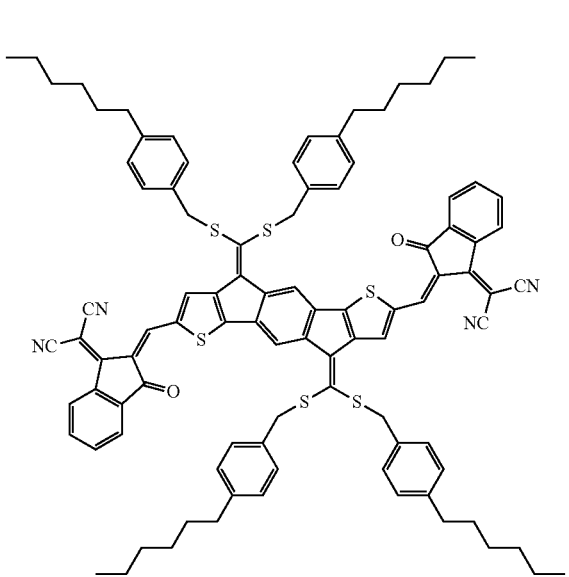

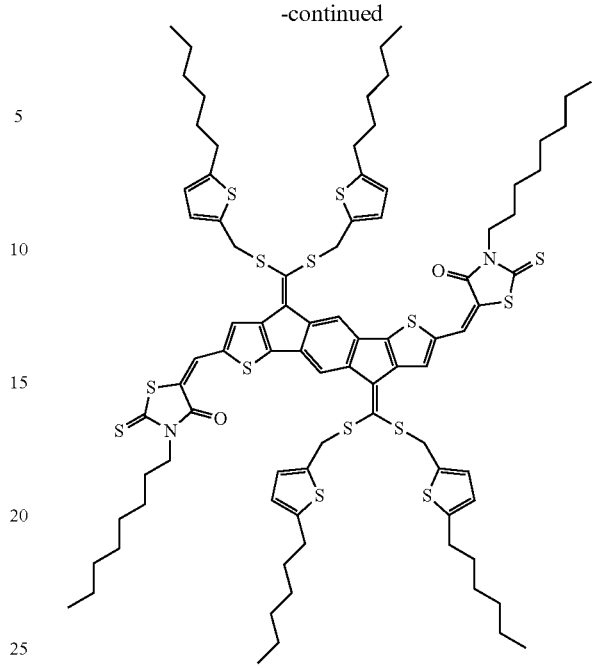

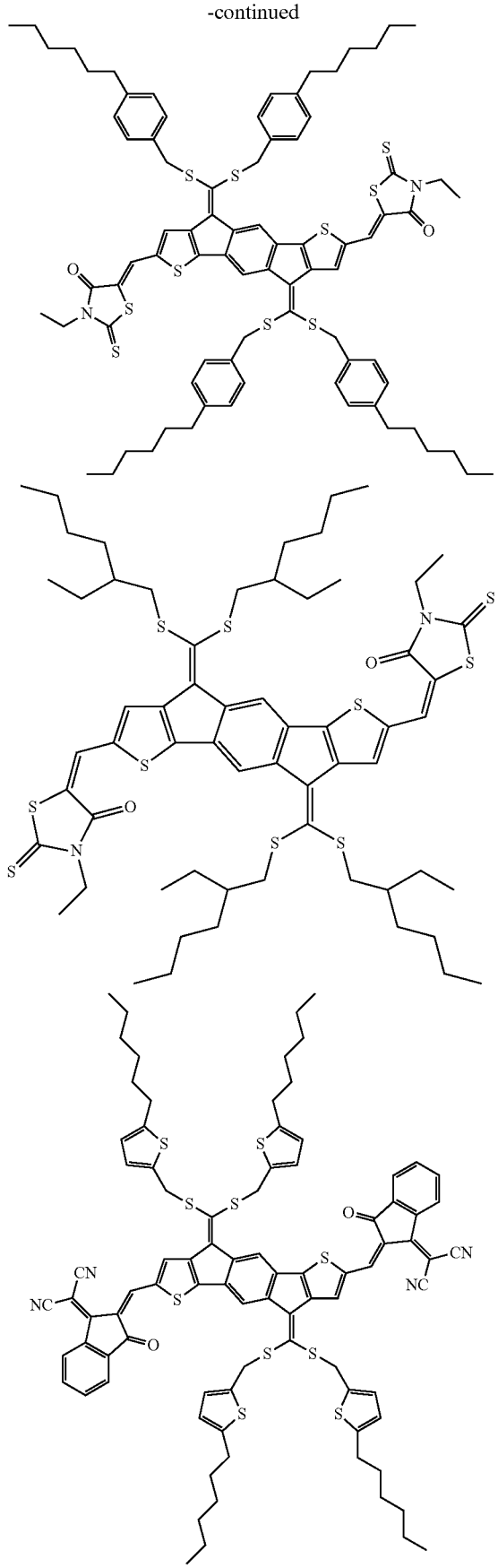

In one embodiment of the present application, the first electrode and the second electrode are not particularly limited as long as they are known in the art. In one embodiment, the first electrode and the second electrode may each independently include indium doped tin oxide (ITO), antimony doped tin oxide (ATO), fluorine doped tin oxide (FTO), indium doped zinc oxide (IZO), ZnO, platinum and the like, but are not limited thereto.

In one embodiment of the present application, the first electrode and the second electrode may each be a transparent electrode. Specifically, ITO having transmittance of 80% or higher may be used.

In one embodiment of the present application, the first electrode and the second electrode each independently have a thickness of 10 nm to 500 nm.

The first electrode or the second electrode may mean a substrate coated with an anode active material commonly used in an electrochromic device. In addition, one example of the substrate may be a current collector. A copper, nickel or SUS current collector may be used depending on a voltage range, and specifically, a copper current collector may be used.

The anode may mean being coated with a common anode active material used in an to electrochromic device, and as types thereof, lithium, metal materials capable of forming an alloy with lithium, transition metal oxides, materials capable of doping or de-doping lithium, materials capable of reversibly intercalating or deintercalating lithium ions, or the like may be used.

More specifically, according to one embodiment of the present application, the first electrode and the second electrode each independently include one or more types of metals selected from the group consisting of lithium (Li), potassium (K), calcium (Ca), sodium (Na), magnesium (Mg), aluminum (Al), zinc (Zn), iron (Fe), nickel (Ni), tin (Sn), lead (Pb), copper (Cu), indium (In), titanium (Ti), vanadium (V) and zirconium (Zr), or alloys thereof.

In addition, specific examples of the transition metal oxide may include vanadium oxides, lithium vanadium oxides and the like, examples of the material capable of doping and de-doping lithium may include Si, SiOx (0<x<2), Si—Y alloys (Y is an alkali metal, an alkali earth metal, a group 13 element, a group 14 element, a transition metal, a rare earth element or a combination thereof, but is not Si), Sn, $SnO_2$, Sn—Y (Y is an alkali metal, an alkali earth metal, a group 13 element, a group 14 element, a transition metal, a rare earth element or a combination thereof, but is not Sn) and the like, or a mixture of at least one thereof and $SiO_2$ may also be used.

Specific examples of the element Y are not particularly limited, but may include Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, or combinations thereof.

The material capable of reversibly intercalating or deintercalating lithium ions is a carbon material, and any carbon-based anode active material generally used in an electrochromic device may be used, and as typical examples, crystalline carbon, amorphous carbon or a combination thereof may be used. Examples of the crystalline carbon may include graphite such as natural graphite or artificial graphite in an amorphous form, a plate form, a flake form, a spherical or fibrous form, and examples of the amorphous carbon may include soft carbon (low temperature baked carbon), hard carbon, mesophase pitch carbide, baked coke and the like.

One embodiment of the present application provides a method for manufacturing an electrochromic device, wherein a method of forming the electrochromic layer is a solution process such as spin coating.

In one embodiment of the present application, the method of forming the electrochromic layer is not particularly limited, and may use methods known in the art. For example, an electroplating method, sputtering, an e-beam evaporation method, a chemical vapor deposition method, a sol-gel coating method or the like may be used.

In one embodiment of the present application, the electrolyte layer may be prepared using materials and methods known in the art. Specifically, a pentaerythritol triacrylate (PETA) monomer, 1 M or higher $LiClO_4$, polycarbonate or the like may be used, however, the material and the method are not limited thereto.

In one embodiment of the present application, a solid electrolyte or a liquid electrolyte may be used as the electrolyte layer, and the electrolyte layer is not particularly limited as long as it is capable of performing a role of migrating ions and electrons.

In one embodiment of the present application, the electrolyte layer may include a lithium salt, a plasticizer, an oligomer, a monomer, an additive, a radical initiator and the like. The oligomer used in the present disclosure needs to have compatibility with the plasticizer.

The degree of bleaching and coloring may be adjusted through changing a thickness of the electrochromic layer, and the layer may be adjusted to be thin when transmittance is required, and adjusted to be thick when opacity is required rather than transparency.

In one embodiment of the present application, the electrochromic layer may have a thickness of greater than or equal to 10 nm and less than or equal to 1.5 μm, and preferably greater than or equal to 20 nm and less than or equal to 1 μm.

One embodiment of the present application provides a method for manufacturing an electrochromic device including preparing a substrate; forming a first electrode on the substrate; forming a second electrode opposite to the first electrode; forming an electrolyte layer between the first electrode and the second electrode; and forming an electrochromic layer between the electrolyte layer and the second electrode, wherein one or more layers of the electrochromic layer include the compound for electrochromism according to Chemical Formula 1.

In the method for manufacturing an electrochromic device, descriptions on the compound for electrochromism used are the same as the descriptions on the compound for electrochromism in the electrochromic device.

In the present application, the method for preparing the compound for electrochromism and the method for manufacturing an electrochromic device including the same will be specifically described in the following preparation examples and examples. However, the following examples are for illustrative purposes only, and the scope of the present specification is not limited thereto.

Preparation Example 1

Preparation of Compound 1

(1) Preparation of Compound A-2

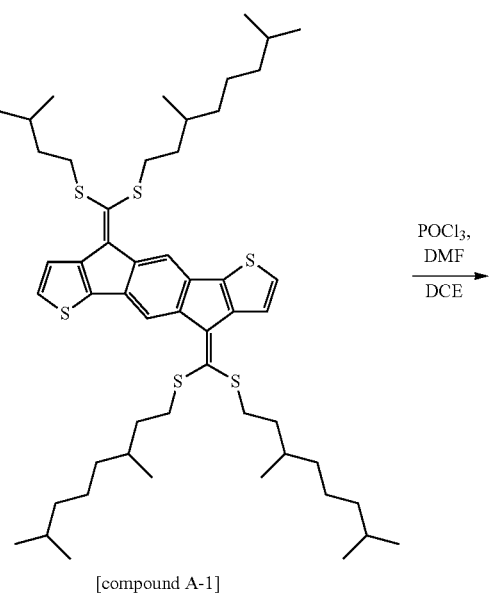

[compound A-1]

21

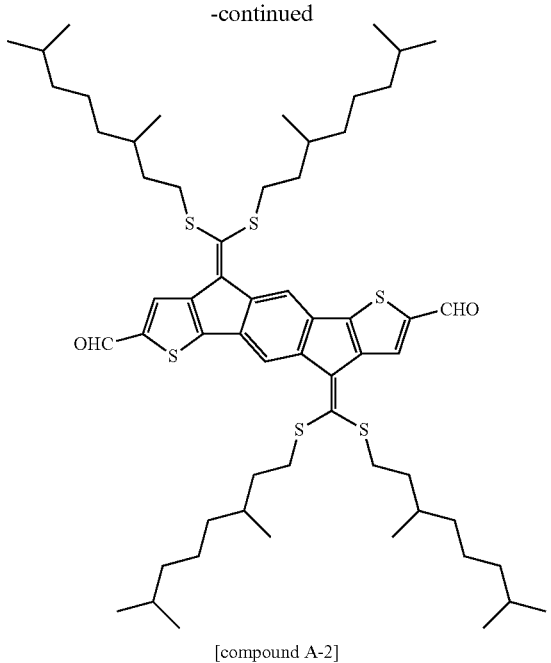

[compound A-2]

1.49 mL of phosphorus oxychloride (POCl$_3$) (16 mmol) was added to 1.55 mL of N,N-dimethylformamide (DMF) (20 mmol), and the result was stirred for 60 minutes at 0° C. to prepare a mixture solution. To the prepared mixture solution, a solution dissolving Compound A-1 (1.53 mmol) in 20 mL of dichloroethane (DCE) was added, and the result was stirred for 48 hours at 100° C. After the stirring, 1 M sodium hydroxide (NaOH) was added thereto, and the result was stirred for 1 hour for neutralization. After that, the result was extracted with dichloromethane, and the extract was dried with anhydrous magnesium sulfate (anhydrous MgSO$_4$) and evaporated. The solvent was removed under vacuum, and then the residue was purified through flash chromatography using hexane and chloroform as an eluent (hexane:chloroform=4:1) to obtain 1.066 g of Compound A-2. (Yield: 67.3%)

Figure 2:
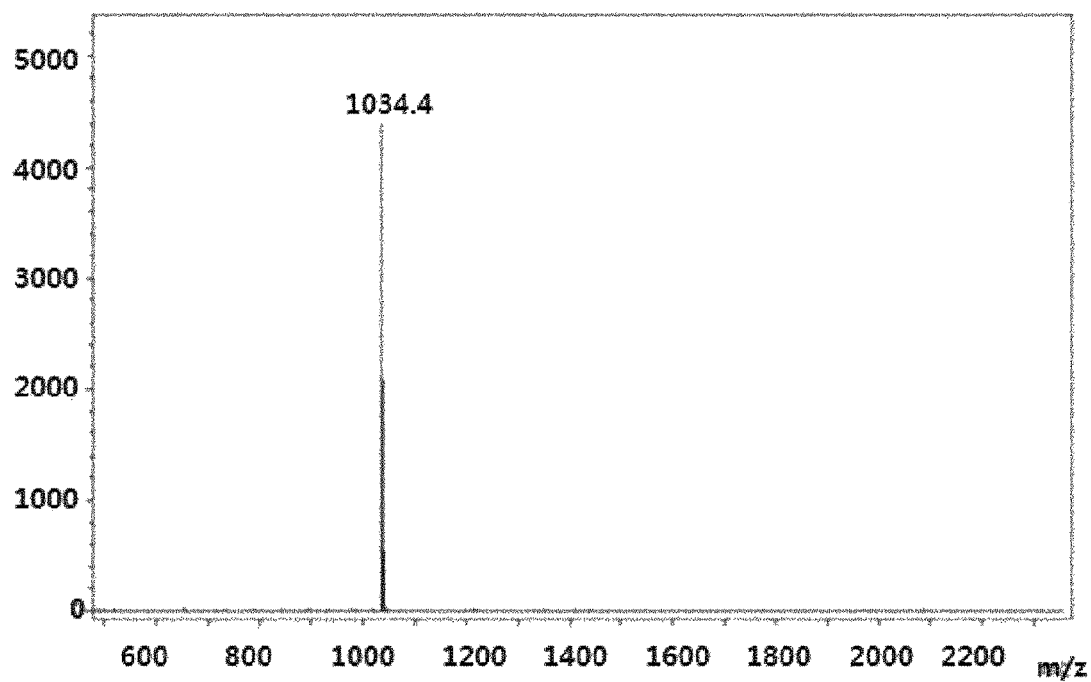
FIG. 2 is a diagram showing an MS spectrum of Compound A-2.

FIG. 2 is a diagram showing an MS spectrum of Compound A-2.

22

(2) Preparation of Compound 1

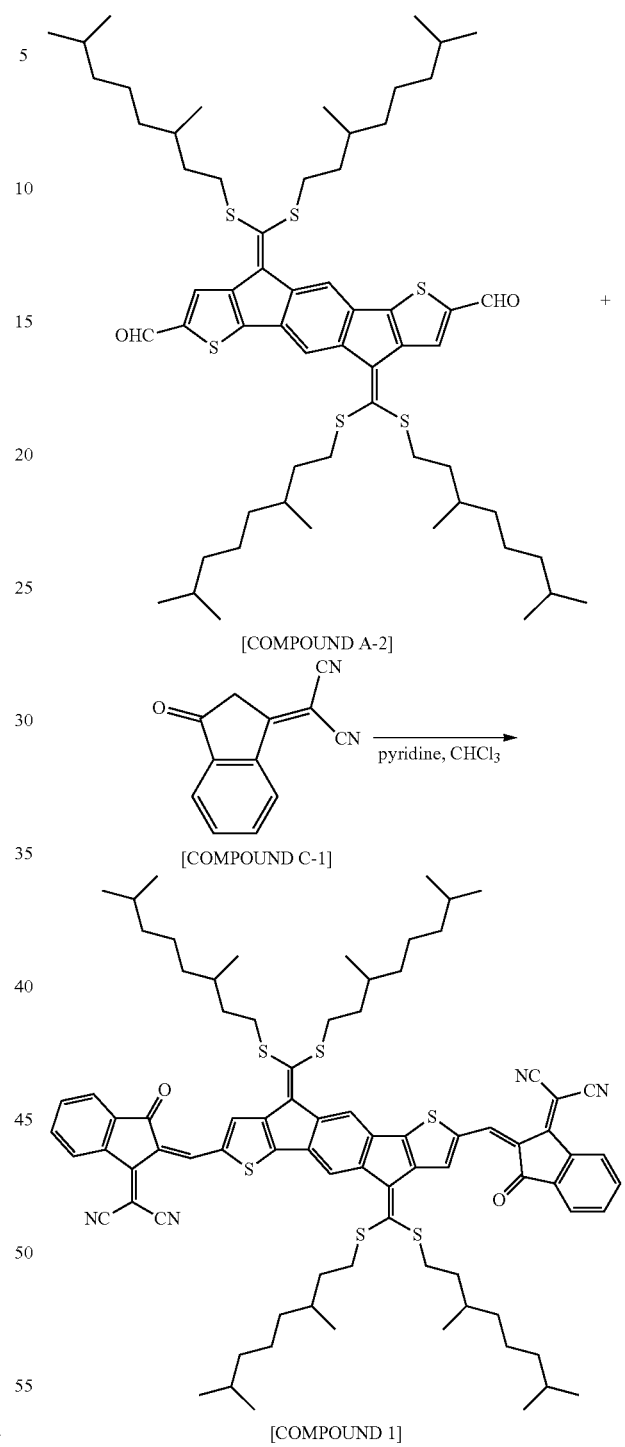

Under nitrogen (N$_2$) atmosphere, 2 mL of pyridine was added to a solution mixing Compound A-2 (0.725 g, 0.7 mmol) and Compound C-1 (0.68 g, 3.5 mmol) in 40 mL of chloroform (CHCl$_3$). After refluxing this mixture solution for 24 hours under nitrogen atmosphere, the solution was extracted with dichloromethane (CH$_2$Cl$_2$) and washed with water. After removing the solvent, the result was recrystallized through methyl chloride (MC)/methanol, and the product was purified through chromatography using a silica gel column using hexane, acetone, ethyl acetate and chloroform (CHCl$_3$) as an eluent. The produced solids were recrystallized through chloroform. After that, the result was washed with methanol and dried under a vacuum condition to obtain 905 mg of Compound 1. (Yield: 93%)

Figure 3:
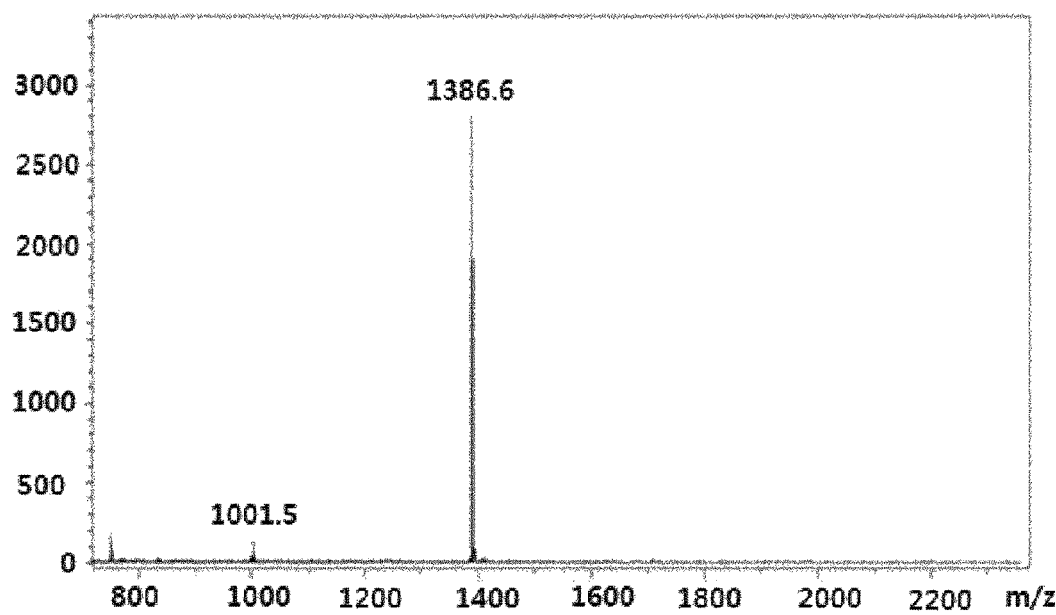
FIG. 3 is a diagram showing an MS spectrum of Compound 1.

FIG. 3 is a diagram showing an MS spectrum of Compound 1.

Preparation Example 2

Preparation of Compound 2

(1) Preparation of Compound B-2

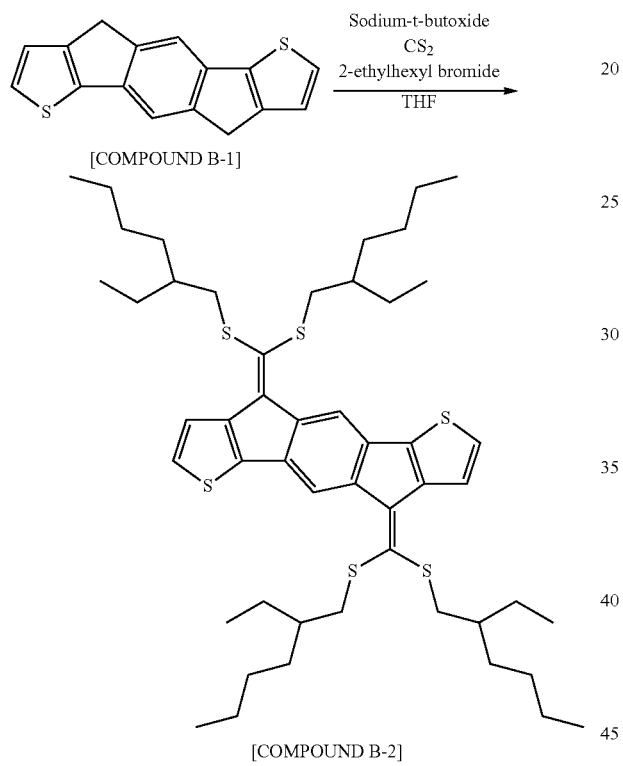

[COMPOUND B-2]

After adding sodium-t-butoxide (NaOC(CH$_3$)$_3$) (4.13 g, 43 mmol) to Compound B-1 (2.5 g, 9.4 mmol)-dissolved tetrahydrofuran (THF) (100 mL), total 2.58 mL of carbon disulfide (CS$_2$) (43 mmol) was added thereto over one hour. After that, 2-ethylhexyl bromide (8.89 mL, 50 mmol) was added thereto, and the result was stirred for 24 hours. After the reaction, ammonium hydroxide (NH$_4$OH) was added thereto to terminate the reaction, the result was extracted with dichloromethane (DCM), and then washed 3 times with water. The product was purified through chromatography using a silica gel column using hexane as an eluent to obtain 3.63 g of Compound B-2 in a red oil form. (Yield: 45%)

Figure 4:
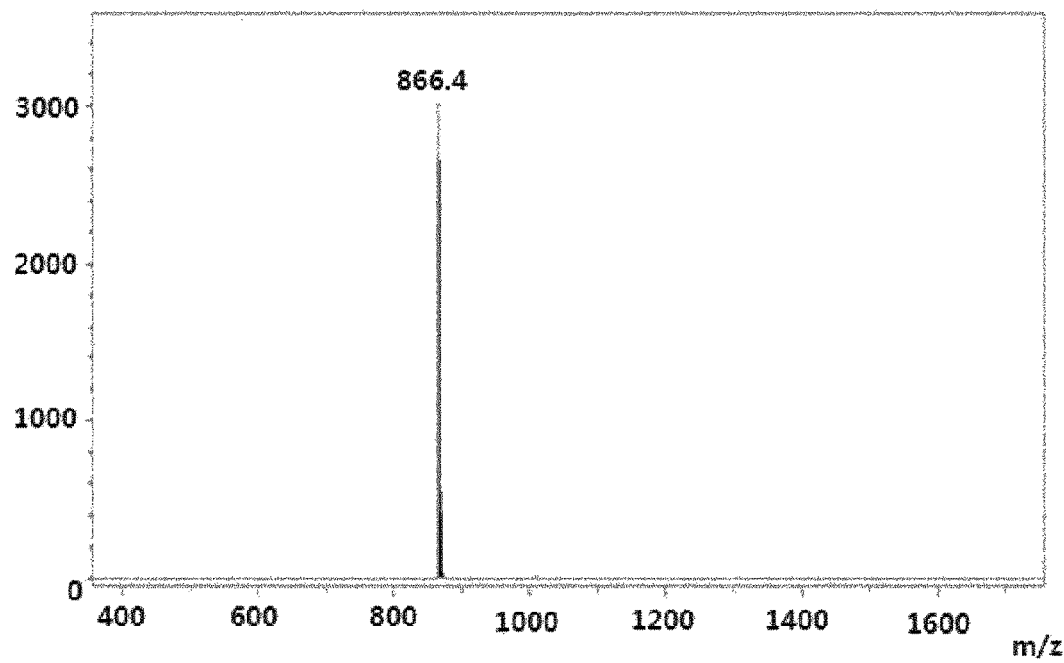
FIG. 4 is a diagram showing an MS spectrum of Compound B-2.

FIG. 4 is a diagram showing an MS spectrum of Compound B-2.

(2) Preparation of Compound B-3

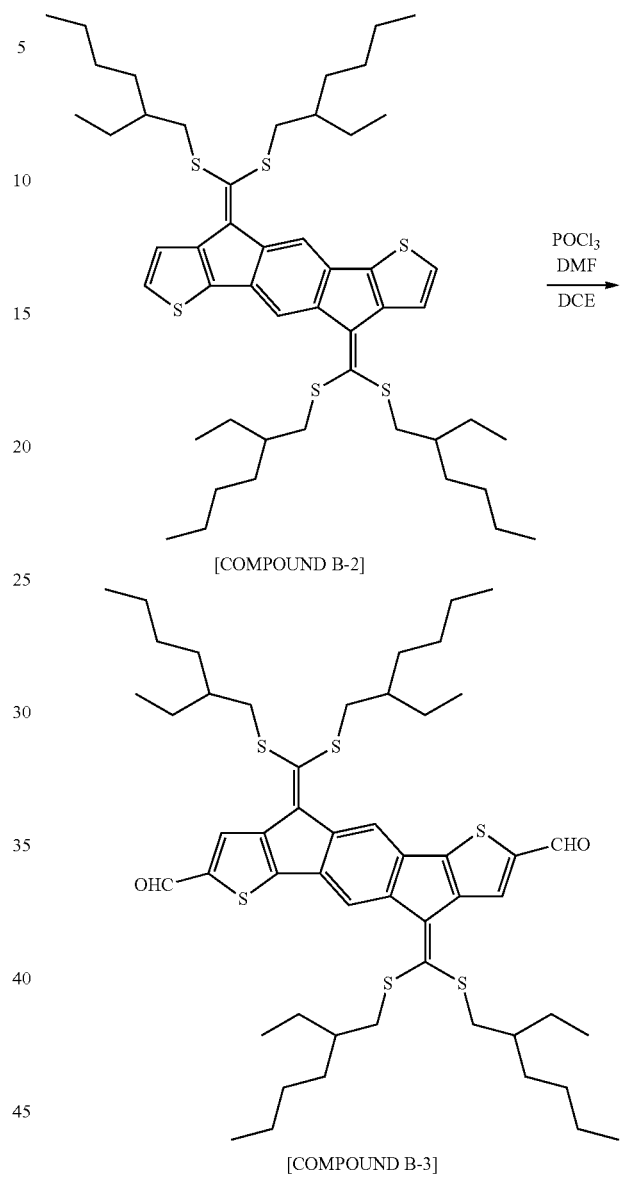

[COMPOUND B-3]

4 mL of phosphorus oxychloride (POCl$_3$) (43 mmol) was added to N,N-dimethylformamide (DMF) (55 mmol), and the result was stirred for 60 minutes at 0° C. to prepare a mixture solution. To the prepared mixture solution, a solution dissolving Compound B-2 (4.19 mmol) in 40 mL of dichloroethane (DCE) was added, and the result was stirred for 48 hours at 100° C. After the stirring, 1 M sodium hydroxide (NaOH) was added thereto, and the result was stirred for 1 hour for neutralization. After that, the result was extracted with dichloromethane, and the extract was dried with anhydrous magnesium sulfate (anhydrous MgSO$_4$) and evaporated. The solvent was removed under vacuum, and then the residue was purified through flash chromatography using hexane and chloroform as an eluent (hexane:chloroform=4:1) to obtain 2.47 g of Compound B-3. (Yield: 64%)

Figure 5:
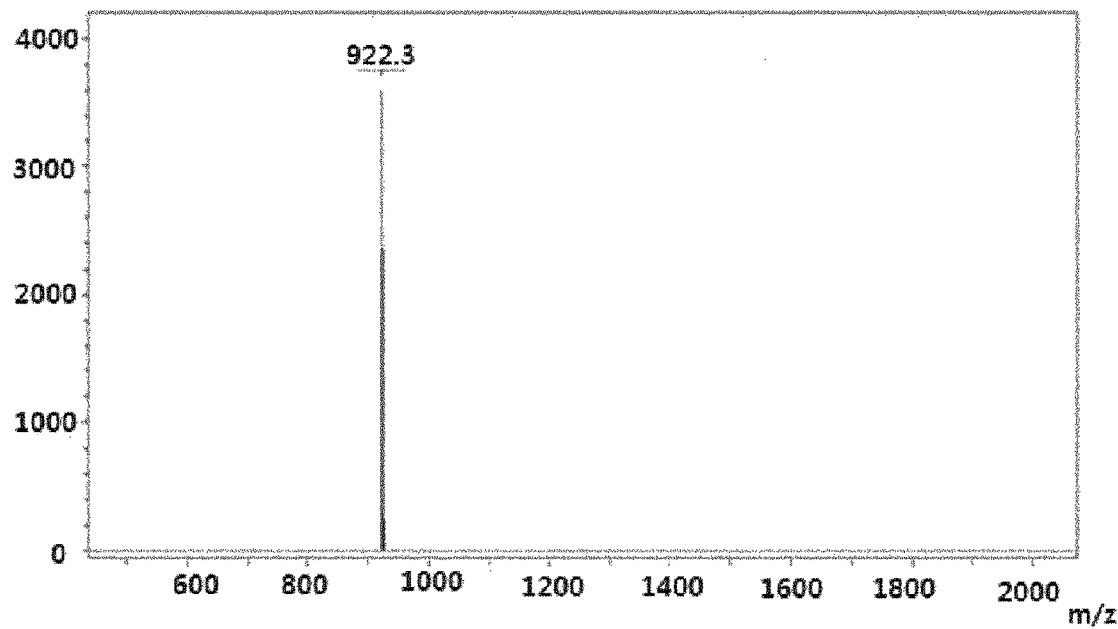
FIG. 5 is a diagram showing an MS spectrum of Compound B-3.

FIG. 5 is a diagram showing an MS spectrum of Compound B-3.

(3) Preparation of Compound 2

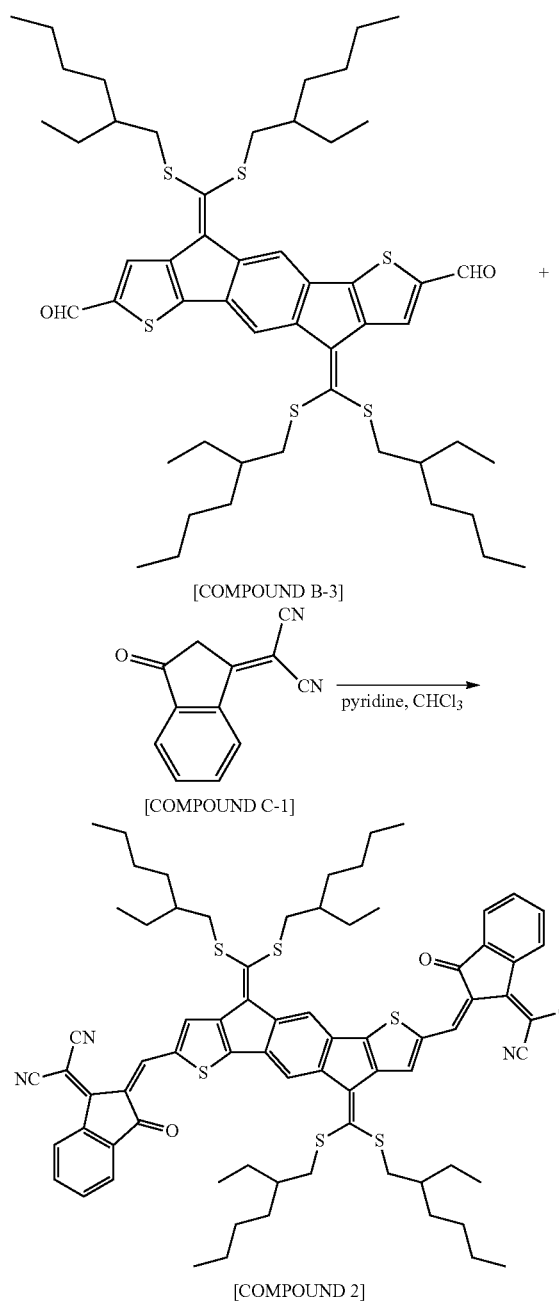

[COMPOUND B-3]

[COMPOUND C-1]

[COMPOUND 2]

Under nitrogen (N₂) atmosphere, 2 mL of pyridine was added to a solution mixing Compound B-3 (0.44 g, 0.48 mmol) and Compound C-1 (0.93 g, 4.8 mmol) in 30 mL of chloroform (CHCl₃). After refluxing this mixture solution for 24 hours under nitrogen atmosphere, the solution was extracted with dichloromethane (CH₂Cl₂) and washed with water. After removing the solvent, the result was recrystallized through methyl chloride (MC)/methanol, and the product was purified through chromatography using a silica gel column using hexane, ethyl acetate and chloroform (CHCl₃) as an eluent. The produced solids were recrystallized through chloroform. After that, the result was washed with methanol and dried under a vacuum condition to obtain 550 mg of Compound 2. (Yield: 90%)

Figure 6:
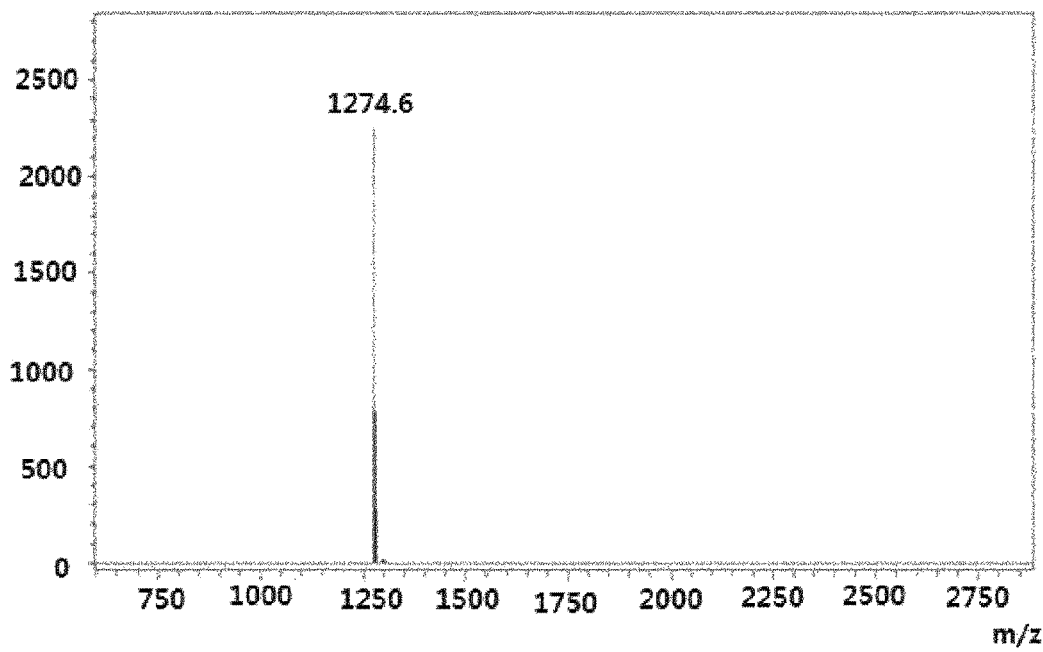
FIG. 6 is a diagram showing an MS spectrum of Compound 2.

FIG. 6 is a diagram showing an MS spectrum of Compound 2.

Preparation Example 3

Preparation of Compound 3

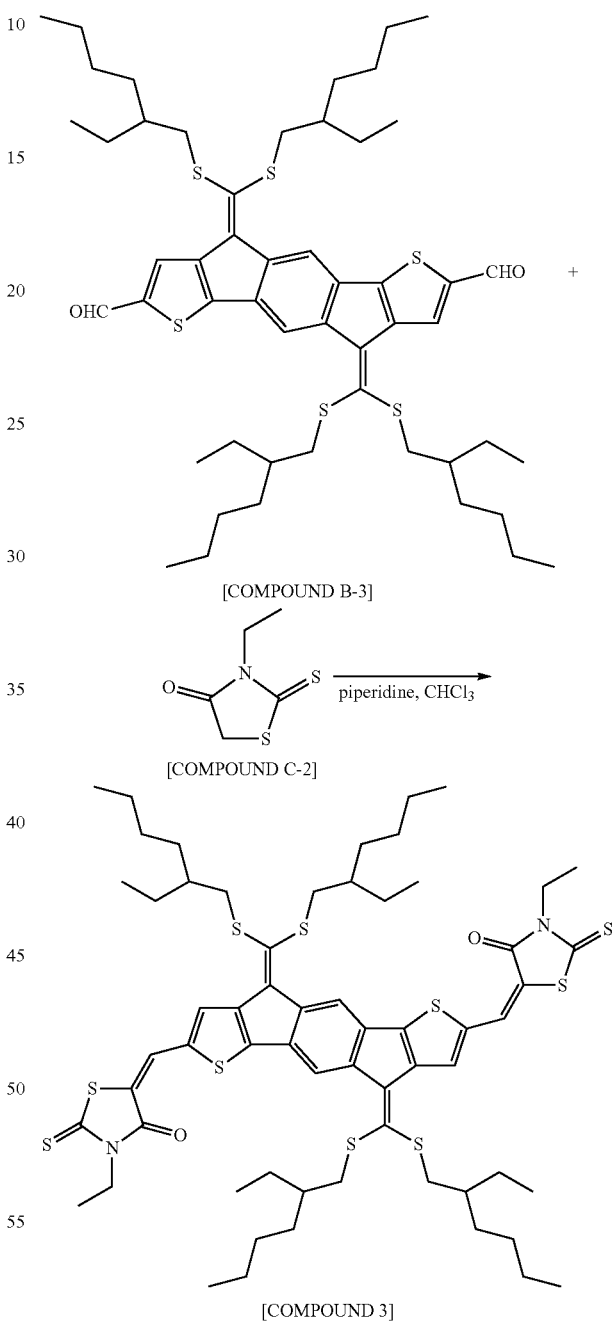

[COMPOUND B-3]

[COMPOUND C-2]

[COMPOUND 3]

Under nitrogen (N₂) atmosphere, three drops of piperidine were added to a solution mixing Compound B-3 (0.83 g, 0.9 mmol) and Compound C-2 (1.45 g, 9 mmol) in 15 mL of chloroform (CHCl₃). After refluxing this mixture solution for 24 hours under nitrogen atmosphere, the solution was extracted with dichloromethane (CH₂Cl₂) and washed with water. After removing the solvent, the result was recrystallized through methyl chloride (MC)/methanol, and the product was purified through chromatography using a silica gel column using hexane, ethyl acetate and chloroform (CHCl$_3$) as an eluent. The produced solids were recrystallized through chloroform. After that, the result was washed with methanol and dried under a vacuum condition to obtain 918 mg of Compound 3. (Yield: 84.3%) (MALDI-TOF MS: 1208.3 g/mol)

Figure 7:
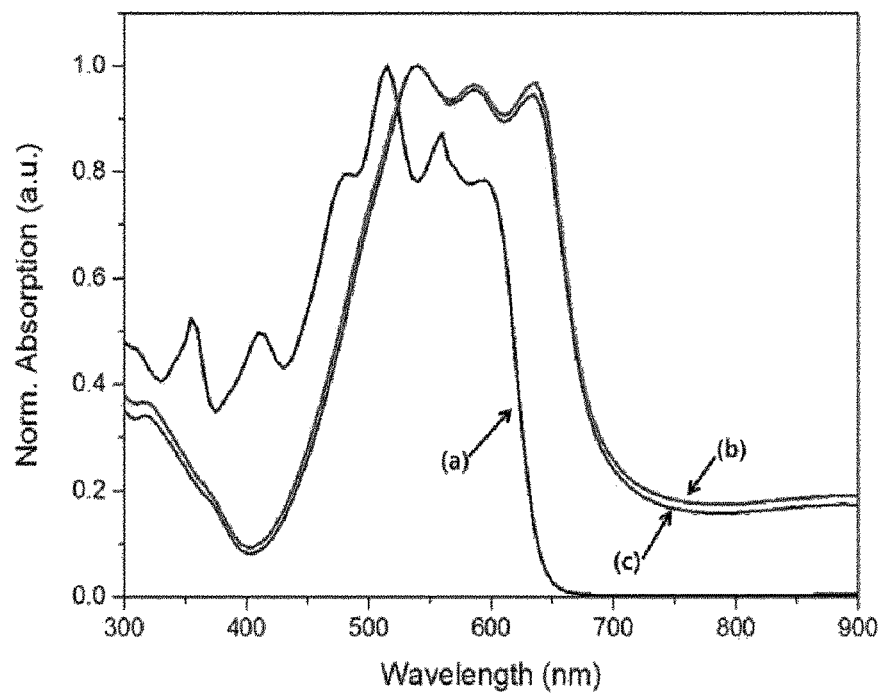
FIG. 7 is a diagram showing UV spectra of Compound 3.

FIG. 7 is a diagram showing UV spectra of Compound 3.

In FIG. 7, (a) shows UV data of Compound 3 in a solution state, (b) shows UV data measuring Compound 3 in a film state, and (c) shows UV data measuring Compound 3 after heat treating for 10 minutes at 110° C. in a film state.

Herein, the solution state is a state in which Compound 3 is dissolved in a chlorobenzene solution, and the film was formed through spin coating Compound 3 in the solution state.

In FIG. 7, it was identified that the vibronic peak of (c) increased after heat treating the film compared to the vibronic peak before heat treating the film. Accordingly, it was identified that crystallinity was superior after the heat treatment.

Figure 8:
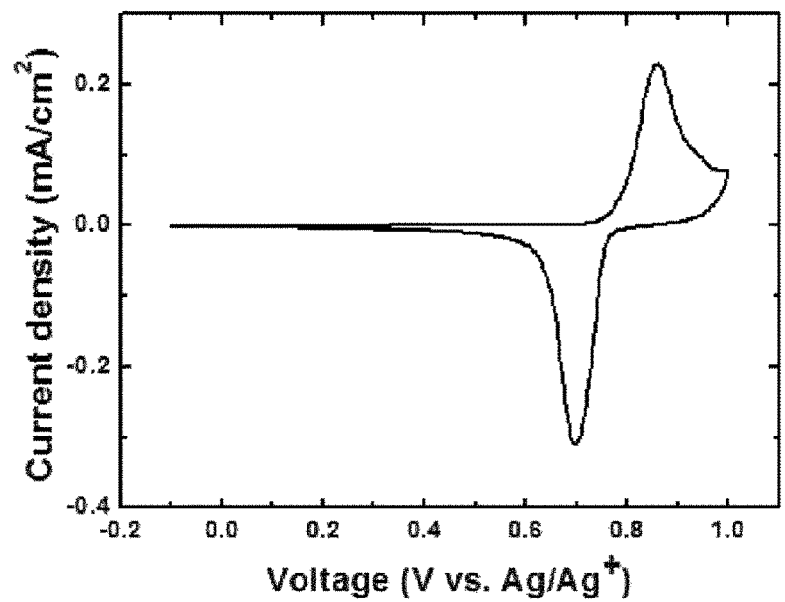
FIG. 8 is a diagram showing a result of measuring CV of Compound 3.

FIG. 8 is a diagram showing a result of measuring CV of Compound 3.

Figure 9:
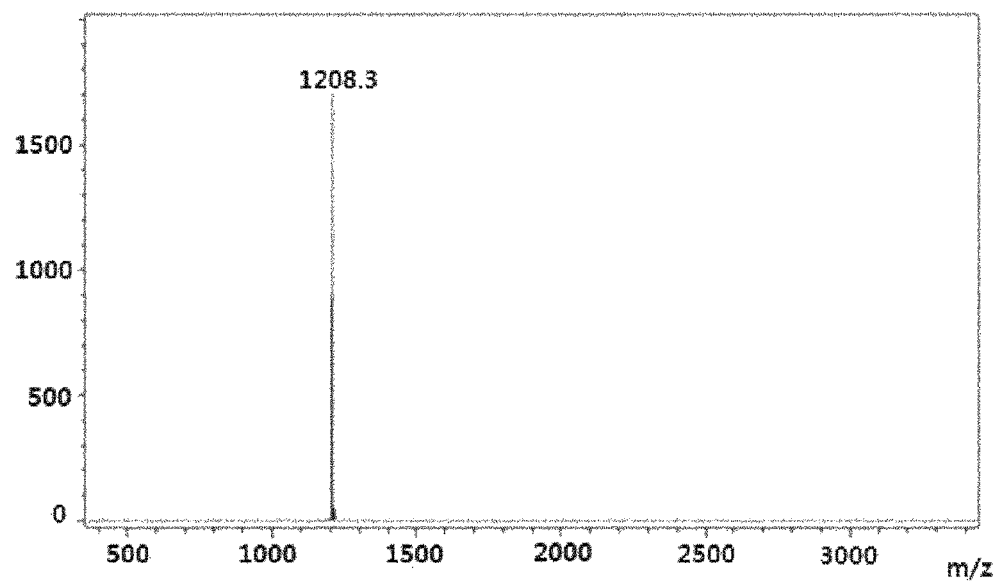
FIG. 9 is a diagram showing an MS spectrum of Compound 3.

FIG. 9 is a diagram showing an MS spectrum of Compound 3.

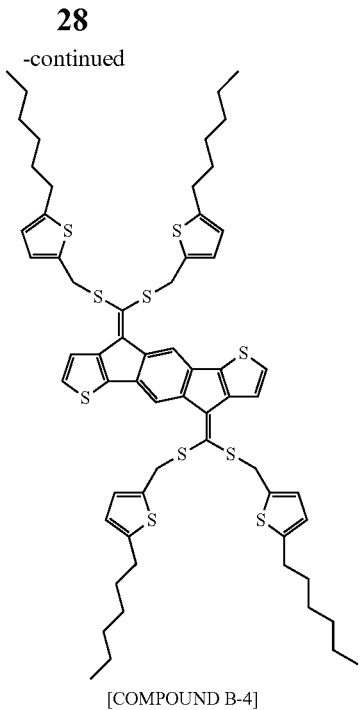

[COMPOUND B-4]

Preparation Example 4

Preparation of Compound 4

(1) Preparation of Compound B-4

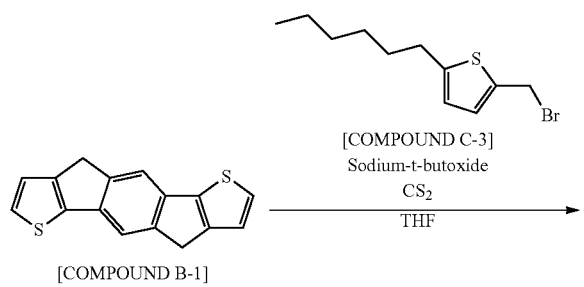

[COMPOUND B-1] → [COMPOUND C-3] Sodium-t-butoxide CS$_2$ THF

After adding sodium-t-butoxide (NaOC(CH$_3$)$_3$) (2.1 g, 21.85 mmol) to a solution dissolving Compound B-1 (1.25 g, 4.7 mmol) in tetrahydrofuran (THF) (100 mL), the result was reacted for 1 hour, and then 1.31 mL of carbon disulfide (CS$_2$) (21.85 mmol) was added thereto. After that, the result was reacted for 1 hour, then Compound C-3 (6.53 g, 25 mmol) was added thereto, and the result was stirred for 24 hours. After the reaction, ammonium hydroxide (NH$_4$OH) was added thereto to terminate the reaction, the result was extracted with dichloromethane (DCM), and then washed 3 times with water. The product was purified through chromatography using a silica gel column using hexane as an eluent to obtain 2.15 g of Compound B-4 in a red viscous oil form. (Yield: 40%) (LCQ MS: 1140.1 g/mol)

(2) Preparation of Compound B-5

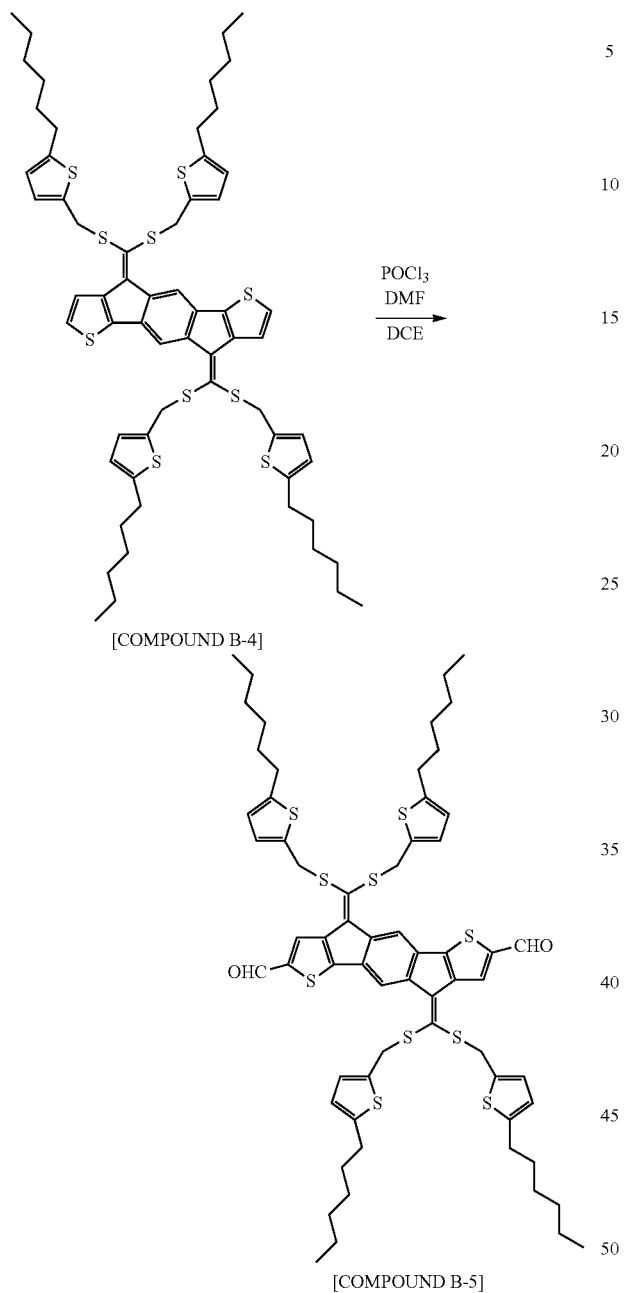

[COMPOUND B-4]

[COMPOUND B-5]

4 mL of phosphorus oxychloride (POCl$_3$) (43 mmol) was added to N,N-dimethylformamide (DMF) (55 mmol), and the result was stirred for 60 minutes at 0° C. to prepare a mixture solution. To the prepared mixture solution, a solution dissolving Compound B-4 (4.77 g, 4.19 mmol) in 40 mL of dichloroethane (DCE) was added, and the result was stirred for 48 hours at 100° C. After the stirring, 1 M sodium hydroxide (NaOH) was added thereto, and the result was stirred for 1 hour for neutralization. After that, the result was extracted with dichloromethane, and the extract was dried with anhydrous magnesium sulfate (anhydrous MgSO$_4$) and evaporated. The solvent was removed under vacuum, and then the residue was purified through flash chromatography using hexane and chloroform as an eluent (hexane:chloroform=4:1) to obtain 4.1 g of Compound B-5. (Yield: 82%) (MALDI-TOF MS: 1196.2 g/mol)

(3) Preparation of Compound 4

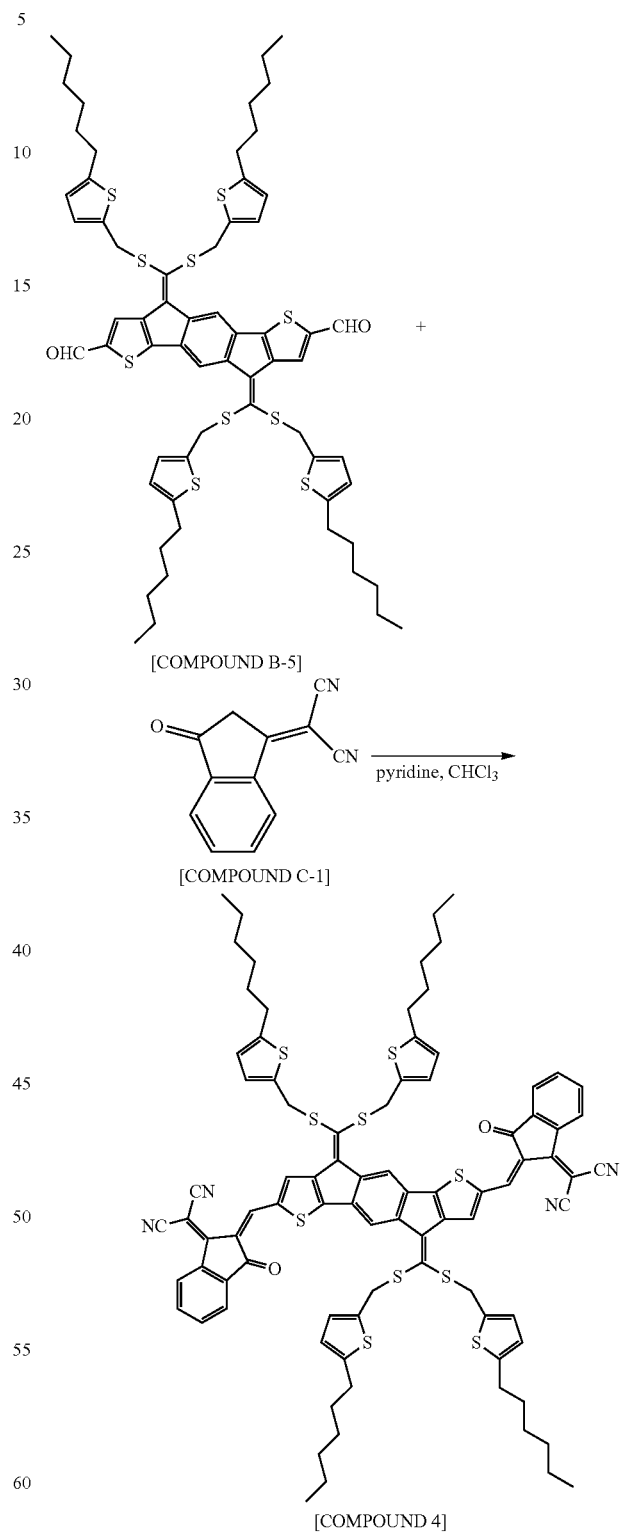

[COMPOUND B-5]

[COMPOUND C-1]

[COMPOUND 4]

Under nitrogen (N$_2$) atmosphere, 2 mL of pyridine was added to a solution mixing Compound B-5 (1 g, 0.84 mmol) and Compound C-1 (1.55 g, 8 mmol) in 30 mL of chloroform (CHCl$_3$). After refluxing this mixture solution for 24 hours under nitrogen atmosphere, the solution was extracted with dichloromethane (CH$_2$Cl$_2$) and washed with water. After removing the solvent, the result was recrystallized through methyl chloride (MC)/methanol, and the product was purified through chromatography using a silica gel column using hexane, ethyl acetate and chloroform (CHCl$_3$) as an eluent. The produced solids were recrystallized through chloroform. After that, the result was washed with methanol and dried under a vacuum condition to obtain 950 mg of Compound 4. (Yield: 73%) (MALDI-TOF MS: 1548.2 g/mol)

Preparation Example 5

Preparation of Compound 5

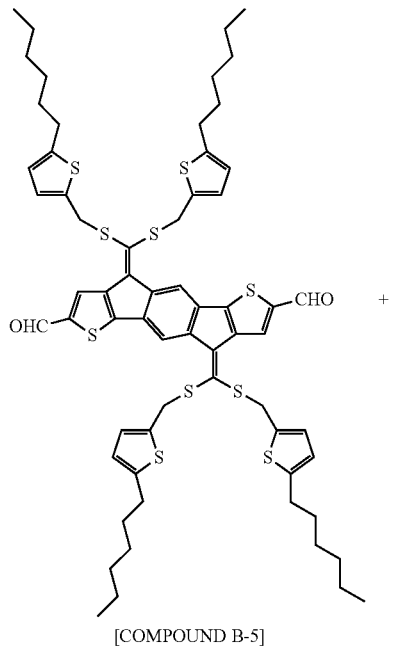

[COMPOUND B-5]

+

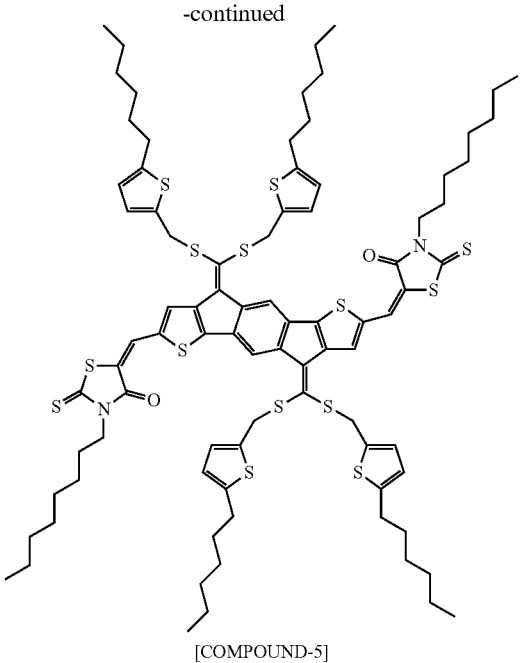

[COMPOUND-5]

Under nitrogen (N$_2$) atmosphere, three drops of piperidine were added to a solution mixing Compound B-5 (1 g, 0.84 mmol) and Compound C-4 (1.96 g, 8 mmol) in 30 mL of chloroform (CHCl$_3$). After refluxing this mixture solution for 24 hours under nitrogen atmosphere, the solution was extracted with dichloromethane (CH$_2$Cl$_2$) and washed with water. After removing the solvent, the result was recrystallized through methyl chloride (MC)/methanol, and the product was purified through chromatography using a silica gel column using hexane, ethyl acetate and chloroform (CHCl$_3$) as an eluent. The produced solids were recrystallized through chloroform. After that, the result was washed with methanol and dried under a vacuum condition to obtain 1.04 g of Compound 5. (Yield: 75%) (MALDI-TOF MS: 1650.6 g/mol)

Preparation Example 6

Preparation of Compound 6

(1) Preparation of Compound B-6

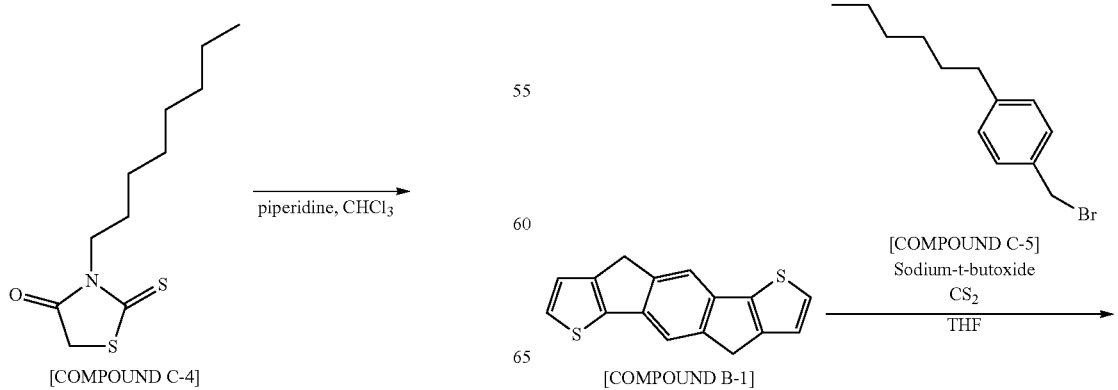

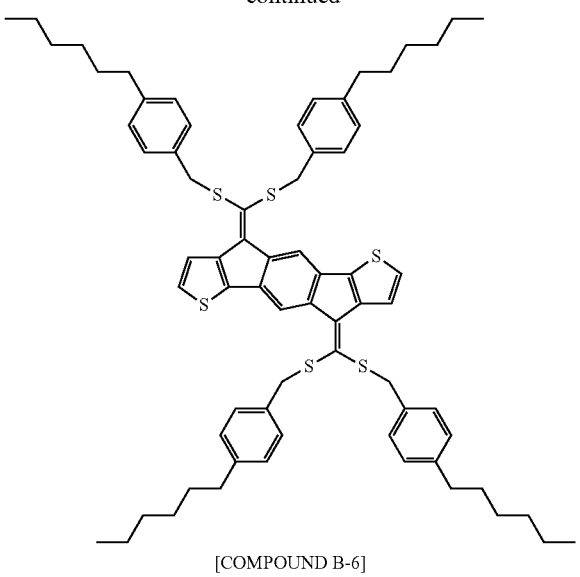

[COMPOUND B-6]

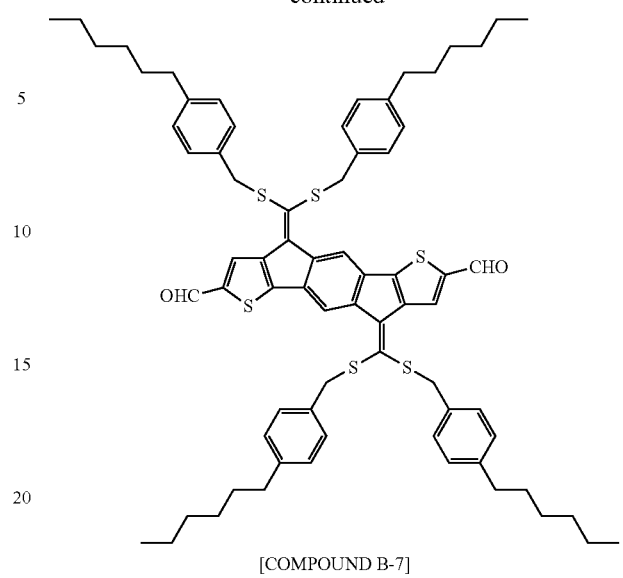

[COMPOUND B-7]

After adding sodium-t-butoxide (NaOC(CH$_3$)$_3$) (2.1 g, 21.85 mmol) to a solution dissolving Compound B-1 (1.25 g, 4.7 mmol) in tetrahydrofuran (THF) (100 mL), the result was reacted for 1 hour. After the reaction, 1.31 mL of carbon disulfide (CS$_2$) (21.85 mmol) was added thereto, and the result was reacted for 1 hour. After that, Compound C-5 (6.38 g, 25 mmol) was added thereto, and the result was stiffed for 24 hours. After the reaction, ammonium hydroxide (NH$_4$OH) was added thereto to terminate the reaction, the result was extracted with dichloromethane (DCM), and then washed 3 times with water. The product was purified through chromatography using a silica gel column using hexane as an eluent to obtain 2.5 g of Compound B-6 in a red viscous oil form. (Yield: 48%) (LCQ MS: 1115.3 g/mol)

(2) Preparation of Compound B-7

4 mL of phosphorus oxychloride (POCl$_3$) (43 mmol) was added to N,N-dimethylformamide (DMF) (55 mmol), and the result was stirred for 60 minutes at 0° C. to prepare a mixture solution. To the prepared mixture solution, a solution dissolving Compound B-6 (4.67 g, 4.19 mmol) in 40 mL of dichloroethane (DCE) was added, and the result was stirred for 48 hours at 100° C. After the stirring, 1 M sodium hydroxide (NaOH) was added thereto, and the result was stirred for 1 hour for neutralization. After that, the result was extracted with dichloromethane, and the extract was dried with anhydrous magnesium sulfate (anhydrous MgSO$_4$) and evaporated. The solvent was removed under vacuum, and then the residue was purified through flash chromatography using hexane and chloroform as an eluent (hexane:chloroform=4:1) to obtain 3.5 g of Compound B-7. (Yield: 71%) (MALDI-TOF MS: 1171.2 g/mol)

(3) Preparation of Compound 6

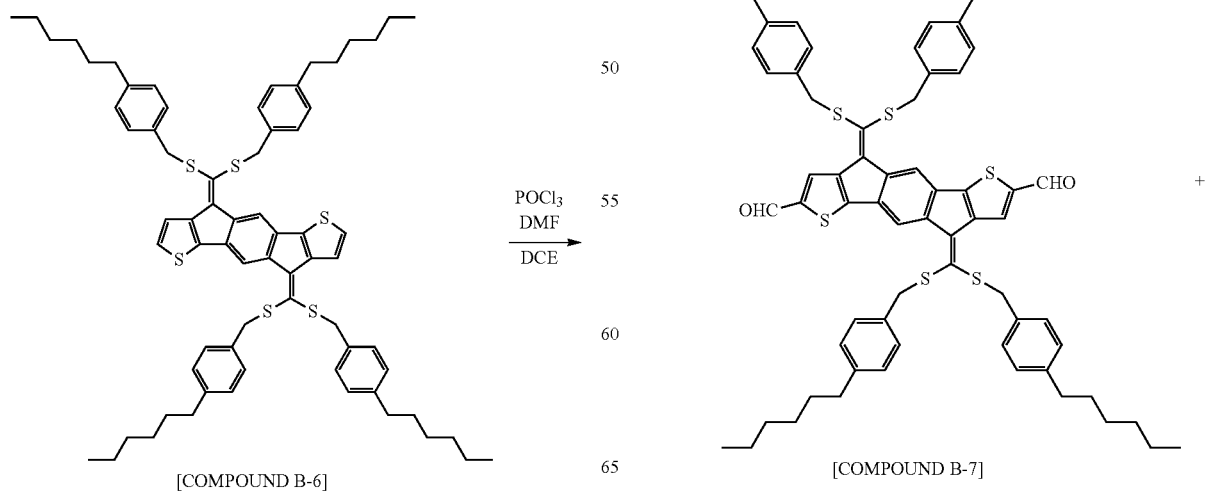

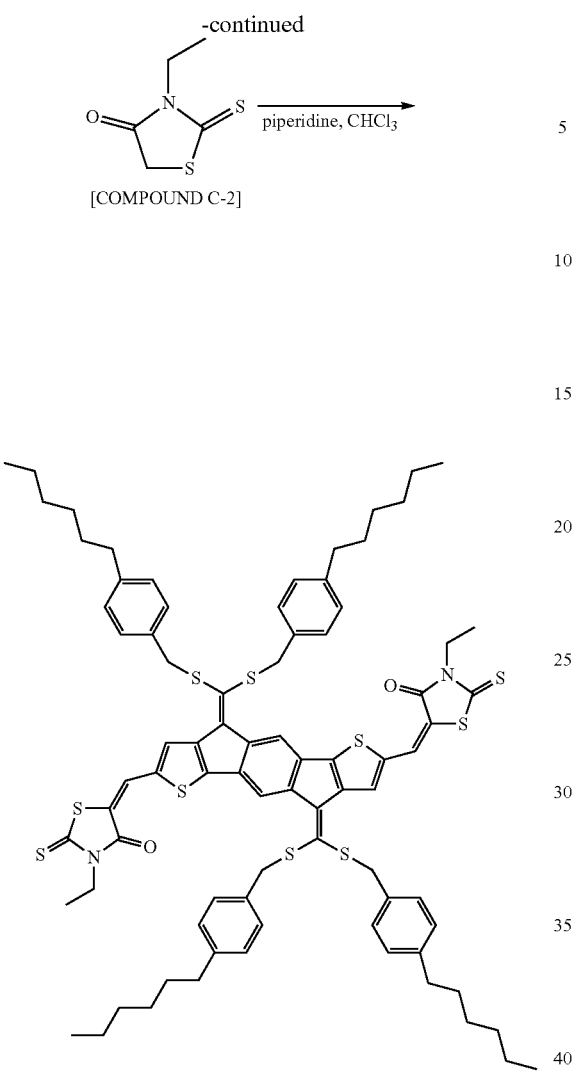

[COMPOUND C-2]

[COMPOUND 6]

Preparation Example 7

Preparation of Compound 7

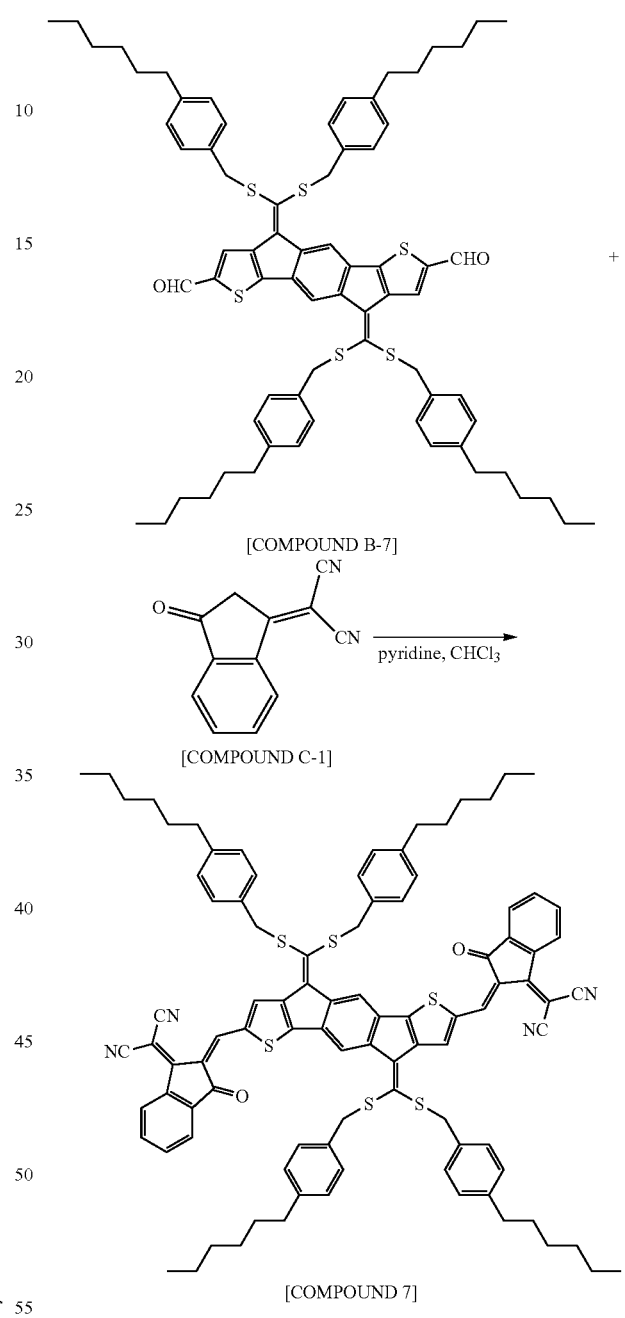

[COMPOUND B-7]

[COMPOUND C-1]

[COMPOUND 7]

Under nitrogen ($N_2$) atmosphere, three drops of piperidine were added to a solution mixing Compound B-7 (1 g, 0.85 mmol) and Compound C-2 (1.29 g, 8 mmol) in 30 mL of chloroform ($CHCl_3$). After refluxing this mixture solution for 24 hours under nitrogen atmosphere, the solution was extracted with dichloromethane ($CH_2Cl_2$) and washed with water. After removing the solvent, the result was recrystallized through methyl chloride (MC)/methanol, and the product was purified through chromatography using a silica gel column using hexane, ethyl acetate and chloroform ($CHCl_3$) as an eluent. The produced solids were recrystallized through chloroform. After that, the result was washed with methanol and dried under a vacuum condition to obtain 970 mg of Compound 6. (Yield: 78%) (MALDI-TOF MS: 1457.6 g/mol)

Under nitrogen ($N_2$) atmosphere, 2 mL of pyridine was added to a solution mixing Compound B-7 (1 g, 0.85 mmol) and Compound C-1 (1.55 g, 8 mmol) in 30 mL of chloroform ($CHCl_3$). After refluxing this mixture solution for 24 hours under nitrogen atmosphere, the solution was extracted with dichloromethane ($CH_2Cl_2$) and washed with water. After removing the solvent, the result was recrystallized through methyl chloride (MC)/methanol, and the product was purified through chromatography using a silica gel column using hexane, ethyl acetate and chloroform ($CHCl_3$) as an eluent. The produced solids were recrystallized through chloroform. After that, the result was washed with methanol and dried under a vacuum condition to obtain 910 mg of Compound 7. (Yield: 70%) (MALDI-TOF MS: 1524.1 g/mol)

Example 1

After dissolving Compound 1 according to Preparation Example 1 in a chloroform solvent in 15 wt %, the result was coated on an indium tin oxide (TTO) substrate, a working electrode, using a sputter, and then dried. As an electrolyte layer, a material dissolving LiClO$_4$ in propylene carbonate was used as the electrolyte, and platinum and silver electrodes were used as a counter electrode and a reference electrode, respectively, to manufacture an electrochromic device.

Examples 2 to 7

An electrochromic device was manufactured in the same manner as in Example 1 except that Compounds 2 to 7 of Preparation Examples 2 to 7 were each used instead of Compound 1 of Preparation Example 1.

Comparative Example 1

An electrochromic device was attempted to be manufactured in the same manner as in Example 1 except that the following Compound K was used instead of Compound 1 of Preparation Example 1, however, the device was not able to be manufactured.

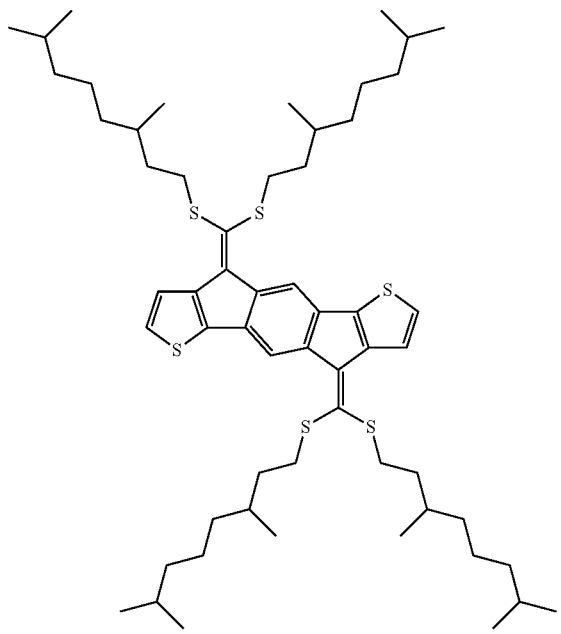

K

Compound K of Comparative Example 1 is a compound having, as a substituent corresponding to Ra and Rb of Chemical Formula 1 of the subject application, hydrogen instead of a group functioning as an electron acceptor, and the compound is in a liquid form having viscosity, and as a result, it was identified that the compound was not suited since an electrochromic device was not able to be manufactured.

Figure 10:
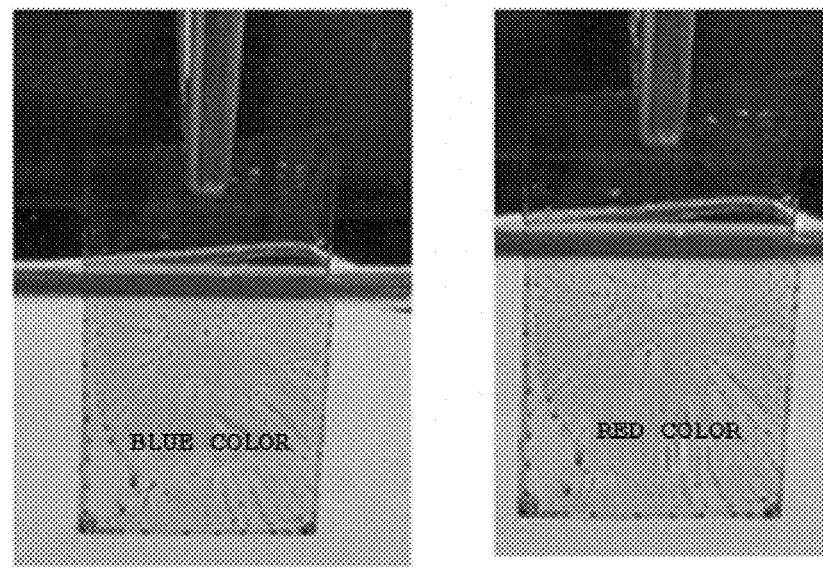
FIG. 10 is a diagram showing an experimental result in an electrochromic device of Compound 3.

FIG. 8 and FIG. 10 are diagrams showing a result of CV measurement and colors when using Compound 3 according to Example 3 in the electrochromic device. It was identified that the electrochromic device using the compound according to one embodiment of the present application exhibited two or more colors depending on the applied voltage.

What is claimed is:
1. An electrochromic device comprising:
a substrate;
a first electrode on the substrate;
a second electrode on the first electrode;
an electrolyte layer between the first electrode and the second electrode; and
an electrochromic layer comprising one or more layers between the electrolyte layer and the second electrode,
wherein the one or more layers of the electrochromic layer comprise a compound for electrochromism of Chemical Formula 1:

[Chemical Formula 1]

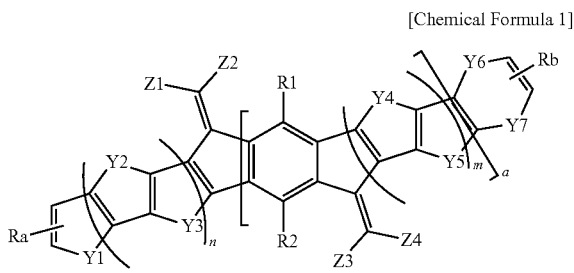

wherein:
Ra and Rb are the same as or different from each other, and each is independently a group functioning as an electron acceptor;
Y1 to Y5 are the same as or different from each other, and each is independently CRR', NR, O, SiRR', PR, S, GeRR', Se or Te;
Y6 and Y7 are different from each other, and each is independently a direct bond, CRR', NR, O, SiRR', PR, S, GeRR', Se or Te;
a is 0 or 1;
when a is 0, Y6 is a direct bond, and Y7 is CRR', NR, O, SiRR', PR, S, GeRR', Se or Te;
when a is 1, Y7 is a direct bond, and Y6 is CRR', NR, O, SiRR', PR, S, GeRR', Se or Te;
n and m are each an integer of 0 to 5;
when n and m are 2 or greater, structures in the parentheses are the same as or different from each other;
Z1 to Z4 are the same as or different from each other, and each is independently CRR'R", NRR', OR, SiRR'R", PRR', SR, GeRR'R", SeR or TeR; and
R1, R2, R, R' and R" are the same as or different from each other, and each is independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heteroaryl group.

2. The electrochromic device of claim 1, wherein the compound of Chemical Formula 1 is a compound of Chemical Formula 2 or 3:

[Chemical Formula 2]

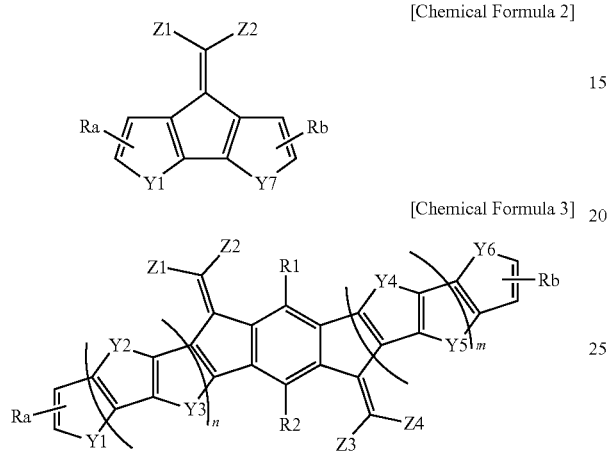

[Chemical Formula 3]

wherein:
Ra and Rb are the same as or different from each other, and each is independently a group functioning as an electron acceptor;
Y1 to Y7 are the same as or different from each other, and each is independently CRR', NR, O, SiRR', PR, S, GeRR', Se or Te;
n and m are each an integer of 0 to 5;
when n and m are 2 or greater, structures in the parentheses are the same as or different from each other;
Z1 to Z4 are the same as or different from each other, and each is independently CRR'R", NRR', OR, SiRR'R", PRR', SR, GeRR'R", SeR or TeR; and
R1, R2, R, R' and R" are the same as or different from each other, and each is independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heteroaryl group.

3. The electrochromic device of claim 2, wherein the compound of Chemical Formula 3 is a compound of Chemical Formula 1-1 or 1-2:

[Chemical Formula 1-1]

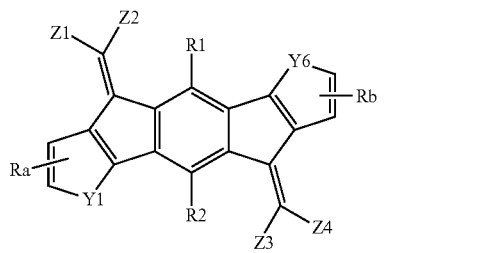

[Chemical Formula 1-2]

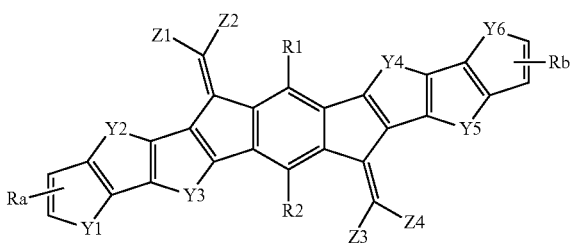

wherein:
Ra and Rb are the same as or different from each other, and each is independently a group functioning as an electron acceptor;
Y1 to Y6 are the same as or different from each other, and each is independently CRR', NR, O, SiRR', PR, S, GeRR', Se or Te;
Z1 to Z4 are the same as or different from each other, and each is independently CRR'R", NRR', OR, SiRR'R", PRR', SR, GeRR'R", SeR or TeR; and
R1, R2, R, R' and R" are the same as or different from each other, and each is independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heteroaryl group.

4. The electrochromic device of claim 1, wherein Ra and Rb are the same as or different from each other, and each is any one of the following structures:

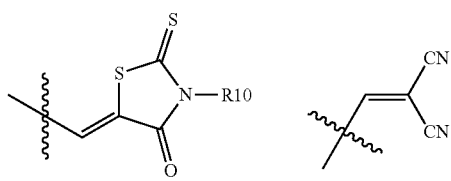

-continued wherein:
c is an integer of 1 to 4;
when c is 2 or greater, structures in the two or more parentheses are the same as or different from each other; and
R10 to R13 are the same as or different from each other, and each is independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heteroaryl group.

5. The electrochromic device of claim 4, wherein R10 to R13 are the same as or different from each other, and each is independently hydrogen or a substituted or unsubstituted alkyl group.

6. The electrochromic device of claim 5, wherein R10 is a substituted or unsubstituted alkyl group.

7. The electrochromic device of claim 4, wherein Ra and Rb are each

R13 is hydrogen, and c is as defined in claim 4.

8. The electrochromic device of claim 4, wherein Ra and Rb are each and R10 is an alkyl group having 1 to 10 carbon atoms.

9. The electrochromic device of claim 1, wherein R1 and R2 are the same as or different from each other, and each is independently hydrogen, a halogen group, a substituted or unsubstituted alkyl group, a substituted or unsubstituted alkoxy group, a substituted or unsubstituted aryl group, or a substituted or unsubstituted heteroaryl group.

10. The electrochromic device of claim 1, wherein R1 and R2 are hydrogen.

11. The electrochromic device of claim 1, wherein Z1 to Z4 are the same as or different from each other and each is independently SR, wherein R is a substituted or unsubstituted alkyl group, a substituted or unsubstituted aryl group, or a substituted or unsubstituted heterocyclic group.

12. The electrochromic device of claim 1, wherein the compound of Chemical Formula 1 is a compound of Chemical Formulae 1-11 to 1-19:

[Chemical Formula 1-11]

[Chemical Formula 1-12]

[Chemical Formula 1-13]
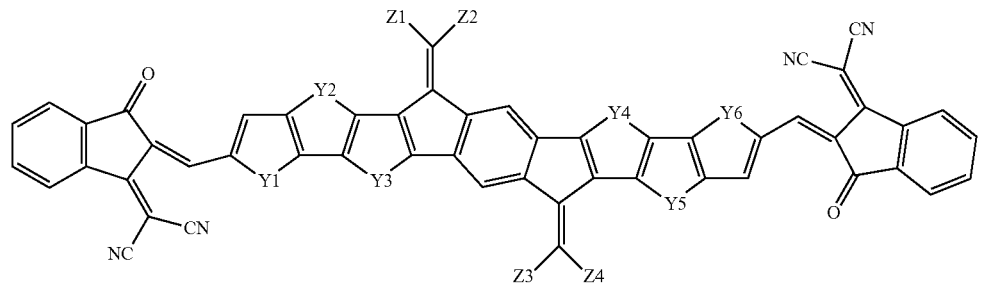
[Chemical Formula 1-14]
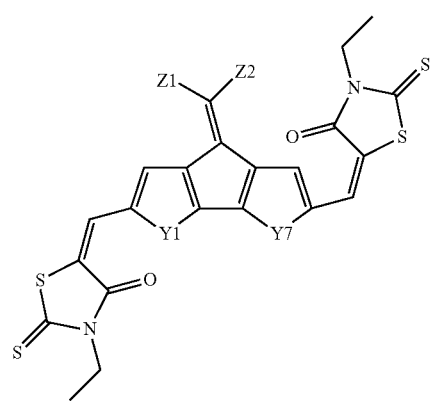
[Chemical Formula 1-15]
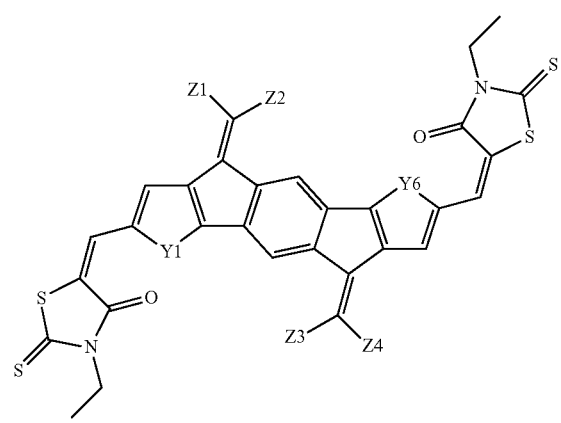
[Chemical Formula 1-16]
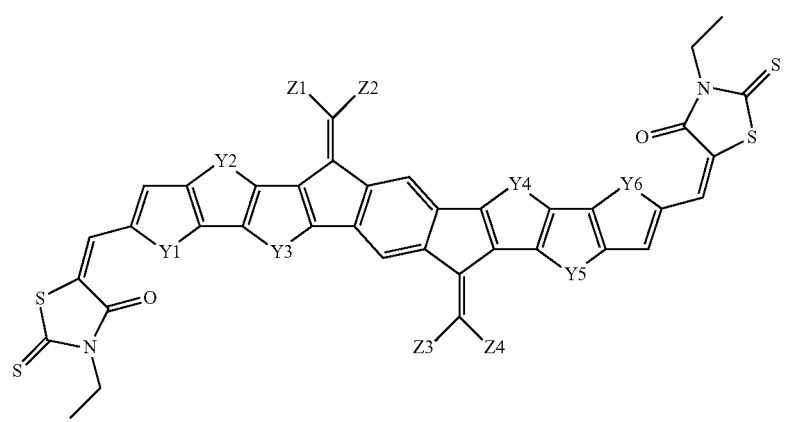

[Chemical Formula 1-17]

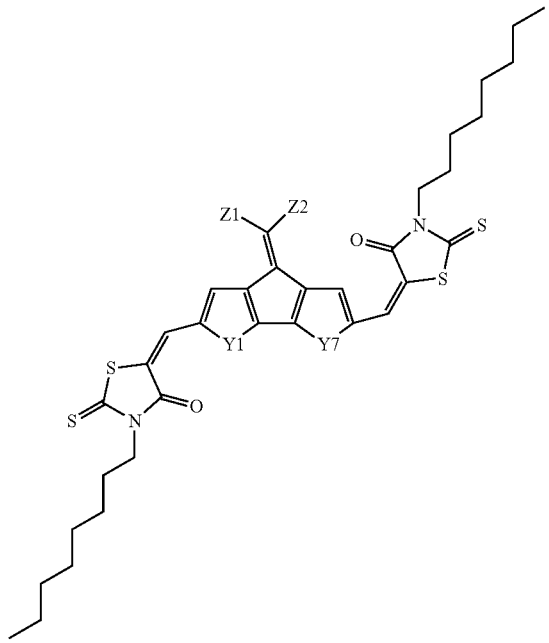

[Chemical Formula 1-18]

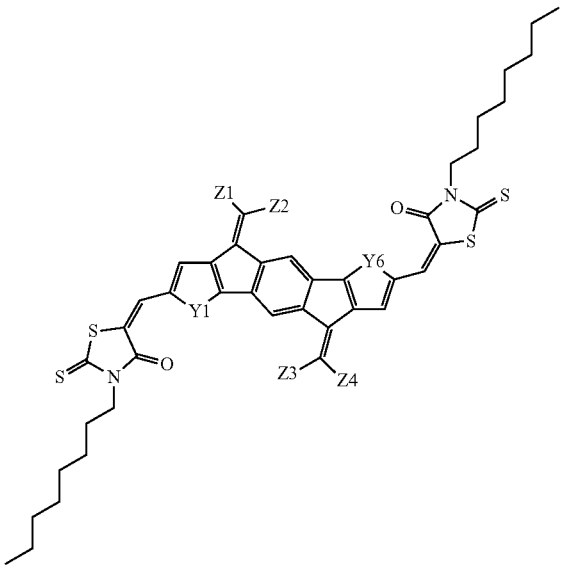

[Chemical Formula 1-19]

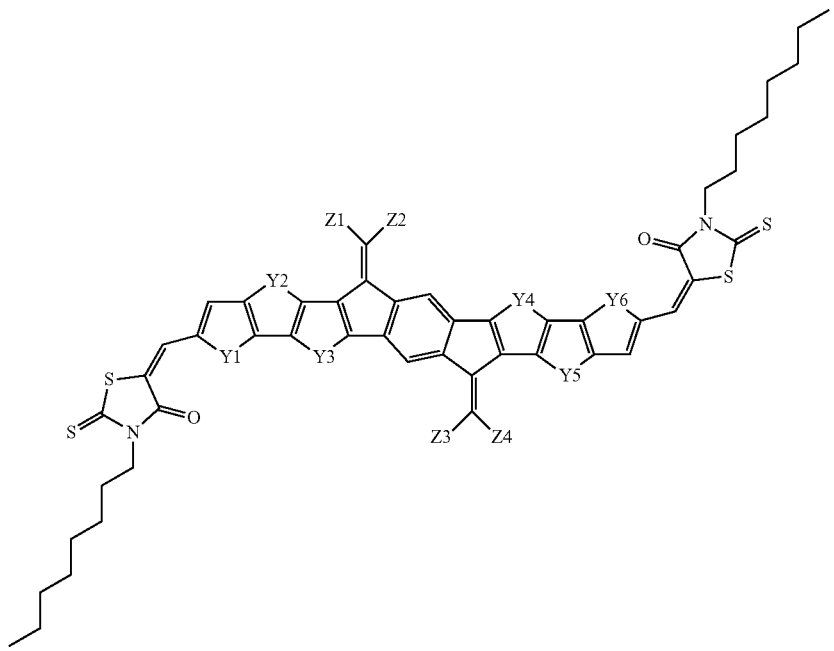

wherein:

Y1 to Y7 are the same as or different from each other, and each is independently CRR', NR, O, SiRR', PR, S, GeRR', Se or Te;

Z1 to Z4 are the same as or different from each other, and each is independently CRR'R", NRR', OR, SiRR'R", PRR', SR, GeRR'R", SeR or TeR; and R, R' and R" are the same as or different from each other, and each is independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group.

13. The electrochromic device of claim 1, wherein the compound of Chemical Formula 1 is any one of the following compounds:
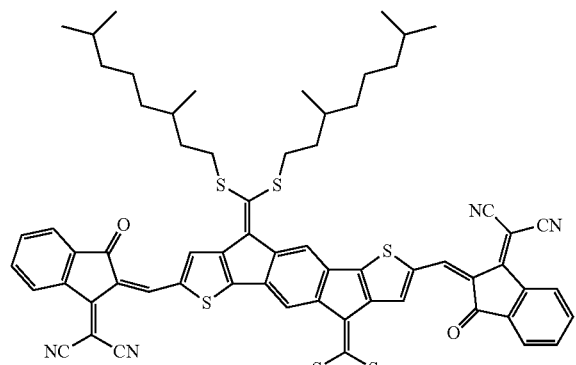
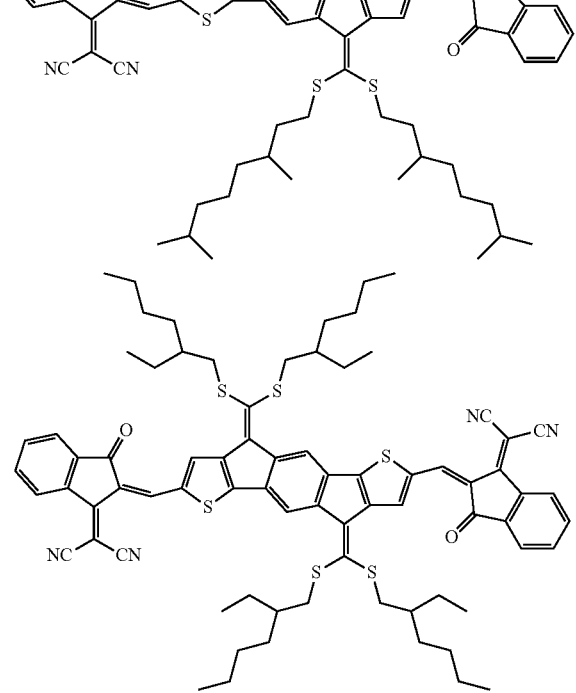
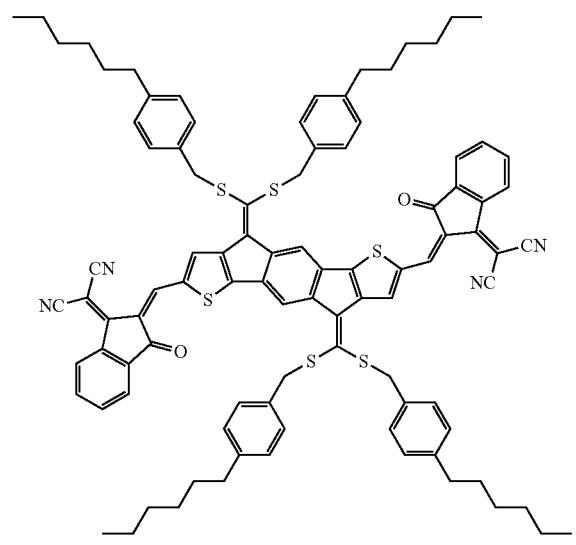
-continued
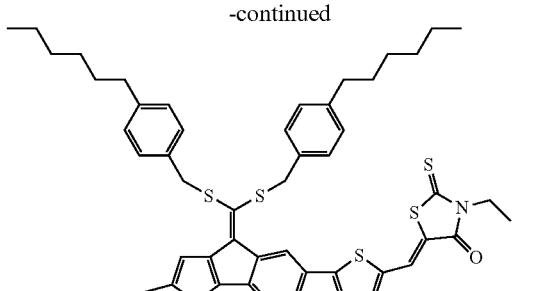
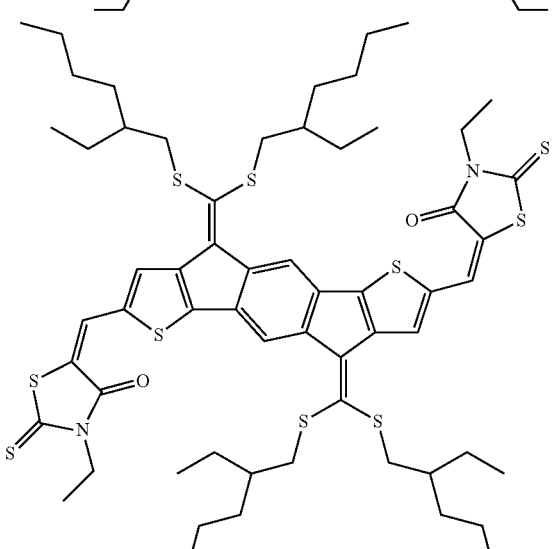
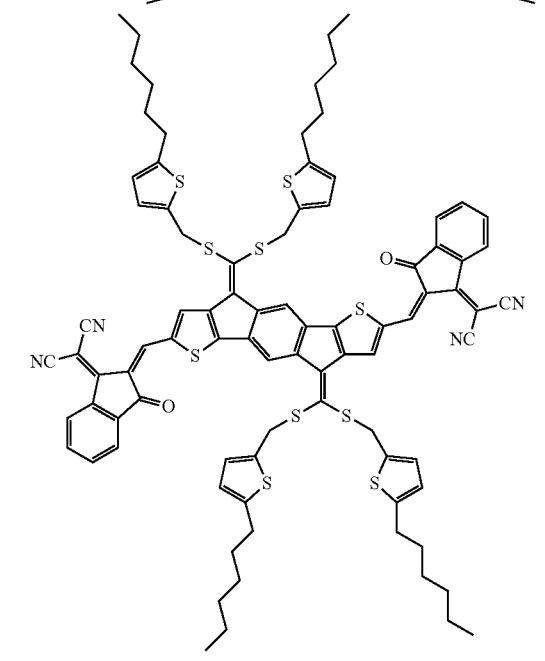

-continued

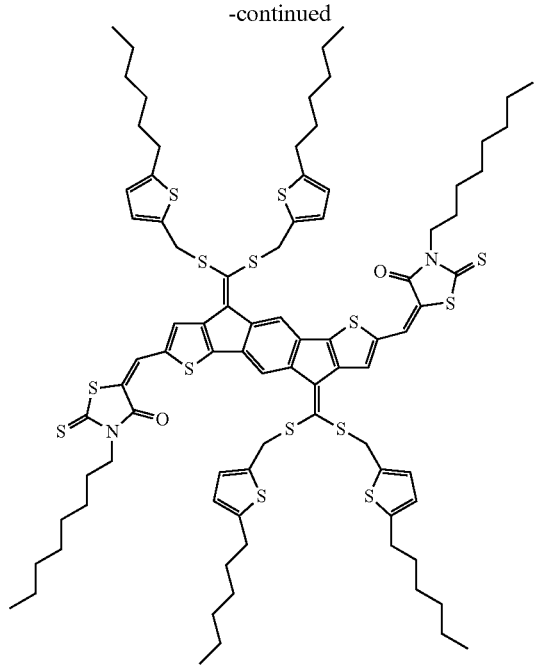

14. The electrochromic device of claim 1, wherein the electrochromic layer has a thickness of 20 nm to 1 μm.

15. A method for manufacturing an electrochromic device comprising:
   providing a substrate;
   forming a first electrode on the substrate;
   forming a second electrode on the first electrode;
   forming an electrolyte layer between the first electrode and the second electrode; and
   forming an electrochromic layer comprising one or more layers between the electrolyte layer and the second electrode,
   wherein the one or more layers of the electrochromic layer comprise a compound for electrochromism of Chemical Formula 1:

[Chemical Formula 1]

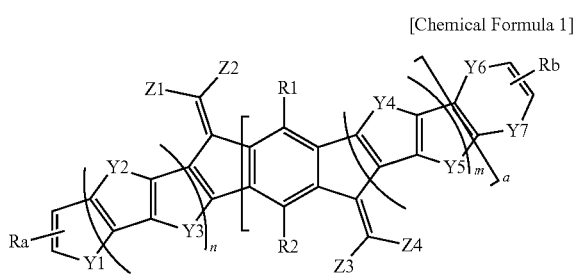

wherein:

Ra and Rb are the same as or different from each other, and each is independently a group functioning as an electron acceptor;

Y1 to Y5 are the same as or different from each other, and each is independently CRR', NR, O, SiRR', PR, S, GeRR', Se or Te;

Y6 and Y7 are different from each other, and each is independently a direct bond, CRR', NR, O, SiRR', PR, S, GeRR', Se or Te;

a is 0 or 1;

when a is 0, Y6 is a direct bond, and Y7 is CRR', NR, O, SiRR', PR, S, GeRR', Se or Te;

when a is 1, Y7 is a direct bond, and Y6 is CRR', NR, O, SiRR', PR, S, GeRR', Se or Te;

n and m are each an integer of 0 to 5;

when n and m are 2 or greater, structures in the parentheses are the same as or different from each other;

Z1 to Z4 are the same as or different from each other, and each is independently CRR'R", NRR', OR, SiRR'R", PRR', SR, GeRR'R", SeR or TeR; and R1, R2, R, R' and R" are the same as or different from each other, and each is independently hydrogen, deuterium, a halogen group, a nitrile group, a nitro group, an imide group, an amide group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heteroaryl group.

16. The method for manufacturing an electrochromic device of claim 15, wherein the forming of the electrochromic layer is carried out with a solution process.

* * * * *